US012674164B2

(12) United States Patent
Marcucci et al.

(10) Patent No.: US 12,674,164 B2
(45) Date of Patent: *Jul. 7, 2026

(54) CONDITIONAL-siRNAs AND USES THEREOF IN TREATING ACUTE MYELOID LEUKEMIA

(71) Applicants:CITY OF HOPE, Duarte, CA (US); CALIFORNIA INSTITUTE OF TECHNOLOGY, Pasadena, CA (US)

(72) Inventors: Guido Marcucci, Duarte, CA (US); Ya-Huei Kuo, Duarte, CA (US); Si-Ping Han, Duarte, CA (US); Lisa Scherer, Duarte, CA (US); William A. Goddard, III, Pasadena, CA (US); John Rossi, Duarte, CA (US)

(73) Assignees: City of Hope, Duarte, CA (US); California Institute of Technology, Pasadena, CA (US)

( * ) Notice: Subject to any disclaimer, the term of this patent is extended or adjusted under 35 U.S.C. 154(b) by 255 days.

This patent is subject to a terminal disclaimer.

(21) Appl. No.: 18/191,623

(22) Filed: Mar. 28, 2023

(65) Prior Publication Data

US 2023/0407308 A1 Dec. 21, 2023

Related U.S. Application Data

(63) Continuation of application No. 16/786,793, filed on Feb. 10, 2020, which is a continuation of application No. PCT/US2018/046383, filed on Aug. 10, 2018.

(60) Provisional application No. 62/543,812, filed on Aug. 10, 2017.

(51) Int. Cl.
*C12N 15/113* (2010.01)

(52) U.S. Cl.
CPC ...... *C12N 15/1135* (2013.01); *C12N 2310/14* (2013.01); *C12N 2310/3519* (2013.01); *C12N 2320/50* (2013.01)

(58) Field of Classification Search
CPC .............. C12N 15/111; C12N 15/1135; C12N 15/1137; C12N 2310/11; C12N 2310/14; C12N 2320/50; C12Y 305/01098
See application file for complete search history.

(56) References Cited

U.S. PATENT DOCUMENTS

| | | | |
|---|---|---|---|
| 6,255,469 B1 | 7/2001 | Seeman et al. |
| 6,506,559 B1 | 1/2003 | Fire et al. |
| 6,566,058 B1 | 5/2003 | Cardy |
| 6,696,285 B1 | 2/2004 | Mills et al. |
| 7,745,594 B2 | 6/2010 | Seelig et al. |
| 8,241,854 B2 | 8/2012 | Yin et al. |

(Continued)

FOREIGN PATENT DOCUMENTS

| | | |
|---|---|---|
| EP | 2101275 A1 | 9/2009 |
| EP | 2213292 B2 | 6/2016 |

(Continued)

OTHER PUBLICATIONS

U.S. Appl. No. 63/172,030, filed Apr. 7, 2021, Han et al.

(Continued)

*Primary Examiner* — Terra C Gibbs
(74) *Attorney, Agent, or Firm* — Dickinson Wright PLLC

(57) ABSTRACT

Disclosed herein are conditional siRNAs activatable by CBFβ-MYH11 oncogenic gene and use thereof for treating conditions such as acute myeloid leukemia (AML). The conditional siRNAs target MCL-1 or HDAC8.

19 Claims, 28 Drawing Sheets

Specification includes a Sequence Listing.

Conventional siRNA

Resistance in cancer cells; cytotoxic side effects in normal cells.

Conditionally activated siRNA

Increased killing of cancer cells; less side effects in normal cells.

(56) References Cited

U.S. PATENT DOCUMENTS

| | | | |
|---|---|---|---|
| 8,318,921 | B2 | 11/2012 | Pierce et al. |
| 8,404,831 | B2 | 3/2013 | Natt et al. |
| 8,710,199 | B2 | 4/2014 | Han et al. |
| 8,962,582 | B2 | 2/2015 | Dirks |
| 9,029,524 | B2 | 5/2015 | Han et al. |
| 9,115,355 | B2 | 8/2015 | Han et al. |
| 9,206,419 | B2 | 12/2015 | Han et al. |
| 9,297,010 | B2 | 3/2016 | Eimen et al. |
| 9,518,263 | B2 | 12/2016 | Han et al. |
| 9,725,715 | B2 | 8/2017 | Han et al. |
| 11,643,659 | B2 | 5/2023 | Marcucci et al. |
| 11,999,954 | B2 | 6/2024 | Han et al. |
| 2005/0079504 | A1 | 4/2005 | Amitai et al. |
| 2009/0234109 | A1 | 9/2009 | Han et al. |
| 2010/0063134 | A1 | 3/2010 | Kaemmerer |
| 2010/0112556 | A1 | 5/2010 | Sampson et al. |
| 2011/0195848 | A1 | 8/2011 | Roopra et al. |
| 2011/0288826 | A1 | 11/2011 | Breaker et al. |
| 2012/0088815 | A1 | 4/2012 | Liang |
| 2012/0101147 | A1 | 4/2012 | Tsai et al. |
| 2013/0244327 | A1 | 9/2013 | Puri et al. |
| 2013/0330725 | A1 | 12/2013 | Saito et al. |
| 2015/0004615 | A1 | 1/2015 | Pierce et al. |
| 2015/0065555 | A1 | 3/2015 | Brown et al. |
| 2015/0284717 | A1 | 10/2015 | Templin et al. |
| 2015/0315581 | A1 | 11/2015 | Han et al. |
| 2016/0046934 | A1 | 2/2016 | Han et al. |
| 2016/0130581 | A1 | 5/2016 | Han et al. |
| 2016/0153036 | A1 | 6/2016 | Chen et al. |
| 2017/0183652 | A1 | 6/2017 | Thum et al. |
| 2018/0092997 | A1 | 4/2018 | Guo et al. |
| 2018/0223344 | A1 | 8/2018 | Chandrasekaran et al. |
| 2019/0153437 | A1 | 5/2019 | Emerick et al. |
| 2019/0233806 | A1 | 8/2019 | Garreau De Loubresse |
| 2020/0291396 | A1 | 9/2020 | Zamore et al. |
| 2021/0019973 | A1 | 1/2021 | Yin et al. |
| 2021/0032707 | A1 | 2/2021 | Talasaz |
| 2021/0095286 | A1 | 4/2021 | Weiss et al. |
| 2021/0123060 | A1 | 4/2021 | Marcucci et al. |
| 2021/0230593 | A1 | 7/2021 | Han et al. |
| 2023/0107117 | A1 | 4/2023 | Das et al. |

FOREIGN PATENT DOCUMENTS

| | | | |
|---|---|---|---|
| EP | 2193140 | B1 | 11/2016 |
| JP | 2018-007663 | A | 1/2018 |
| WO | WO2008076324 | | 6/2008 |
| WO | WO2011/163526 | | 12/2011 |
| WO | WO2013/075132 | | 5/2013 |
| WO | WO2013/142735 | | 9/2013 |
| WO | WO2019/014656 | | 1/2019 |
| WO | WO2019/033079 | | 2/2019 |
| WO | WO2019033083 | | 2/2019 |
| WO | WO2020/033938 | | 2/2020 |
| WO | WO2023/283546 | | 1/2023 |
| WO | WO2023/283548 | | 1/2023 |
| WO | WO2023/283550 | | 1/2023 |
| WO | WO2023/283551 | | 1/2023 |
| WO | WO2023/283552 | | 1/2023 |
| WO | WO2023/283553 | | 1/2023 |
| WO | WO2023/070057 | | 4/2023 |

OTHER PUBLICATIONS

U.S. Appl. No. 63/218,862, filed Jul. 6, 2021, Si-ping Han.
U.S. Appl. No. 63/218,833, filed Jul. 6, 2021, Han et al.
U.S. Appl. No. 63/218,850, filed Jul. 6, 2021, Han et al.
U.S. Appl. No. 63/218,865, filed Jul. 6, 2021, Si-ping Han.
Adams et al., "Patisiran, an RNAi Therapeutic, for Hereditary Transthyretin Amyloidosis," The New England Journal of Medicine 2018, 379(1), 11-21.
Aduri et al., "Amber Force Field Parameters for the Naturally Occurring Modified Nucleosides in RNA," Journal of Chemical Theory and Computation 2007, 3, 1464-1475.

Afonin et al., "Design and self-assembly of siRNA-functionalized RNA nanoparticles for use in automated nanomedicine," Nature Protocols 2011, 6, 2022-2034.
American Cancer Society, "Key Statistics for Acute Myeloid Leukemia (AML)," cancer.org 2023, in 10 pages. https://www.cancer.org/cancer/types/acute-myeloid-leukemia/about/key-statistics.html.
Avino et al., "Oligonucleotide-peptide conjugates: solid-phase synthesis under acidic conditions and use in Elisa assays," Molecules 2012, 17, 13825-13843.
Benenson et al., "An Autonomous Molecular Computer for Logical Control of Gene Expression," Nature 2004, 429, 423-429.
Benenson, "Biomolecular Computing Systems: Principles, Progress and Potential," Nature Reviews Genetics 2012, 13, 455-468.
Beta Lab, "RNAsoft—Software for RNA/DNA secondary structure prediction and design," University of British Columbia 2023, in 1 page. http://www.rnasoft.ca/.
Bhatia et al., "A synthetic icosahedral DNA-based host-cargo complex for functional in vivo imaging," Nature Communications 2011, 2, in 8 pages.
Bindewald et al., "Multistrand Structure Prediction of Nucleic Acid Assemblies and Design of RNA Switches," Nano Letters 2016, 16(3), 1726-1735.
Bobbin & Rossi, "RNA Interference (RNAi)-Based Therapeutics: Delivering on the Promise?" Annual Review of Pharmacology and Toxicology 2016, 56, 103-122.
Boudreau et al., "Rational Design of Therapeutic siRNAs: Minimizing Off-targeting Potential to Improve the Safety of RNAi Therapy for Huntington's Disease," Molecular Therapy 2011, 19(12), 2169-2177.
Bramsen et al., "A Large-Scale Chemical Modification Screen Identifies Design Rules to Generate siRNAs with High Activity, High Stability and Low Toxicity," Nucleic Acids Research 2009, 37(9), 2867-2881.
Bujold et al., "Optimized DNA "Nanosuitcases" for Encapsulation and Conditional Release of siRNA," Journal of the American Chemical Society 2016, 138, 14030-14038.
Camacho et al., "Blast+: Architecture and Applications," BMC Bioinformatics 2009, 10, in 9 pages.
Cao et al., "Histone deacetylase (HDAC) inhibitors attenuate cardiac hypertrophy by suppressing autophagy," Proceedings of the National Academy of Sciences 2011, 108, 4123-4128.
Chatterjee et al., "Nucleic Acid Strand Displacement with Synthetic mRNA Inputs in Living Mammalian Cells," ACS Synthetic Biology 2018, 7(12), 2737-2741.
Chen et al., "DNA Nanotechnology from the Test Tube to the Cell," Nature Nanotechnology 2015, 10, 748-760.
Chojnowski et al., "RNA Bricks—a database of RNA 3D motifs and their interactions," Nucleic Acids Research 2014, 42, D123-D121.
Colasanti et al., "Analyzing and Building Nucleic Acid Structures with 3DNA," Journal of Visualized Experiments 2013, 74, in 10 pages.
Collingwood et al., "Chemical Modification Patterns Compatible with High Potency Dicer-Substrate Small Interfering RNAs," Oligonucleotides 2008, 18, 187-200.
Condon et al., "Optimization of an Amber Force Field for the Artificial Nucleic Acid, LNA, and Benchmarking with NMR of L(CAAU)," The Journal of Physical Chemistry B 2014, 118, 1216-1228.
Dirks et al., "A partition function algorithm for nucleic acid secondary structure including pseudoknots," Journal of Computational Chemistry 2003, 24, 1664-1677.
Dirks et al., "An algorithm for computing nucleic acid base-pairing probabilities including pseudoknots," Journal of Computational Chemistry 2004, 25, 1295-1304.
Dirks et al., "Paradigms for computational nucleic acid design," Nucleic Acids Research 2004, 32, 1392-1403.
Dirks et al., "Thermodynamic analysis of interacting nucleic acid strands," SIAM Review 2007, 49, 65-88.
Dowdy, "Overcoming cellular barriers for RNA therapeutics," Nature Biotechnology 2017, 35(3), 222-229.
Dresselhaus & Meffert, "Cellular specificity of NF-κB function in the nervous system," Frontiers in Immunology 2019, 10, in 14 pages.

(56) References Cited

OTHER PUBLICATIONS

Duan et al., "A Point-Charge Force Field for Molecular Mechanics Simulations of Proteins Based on Condensed-Phase Quantum Mechanical Calculations," Journal of Computational Chemistry 2003, 24, 1999-2012.

Duda et al., "Targeting GSK3 signaling as a potential therapy of neurodegenerative diseases and aging," Expert Opinion on Therapeutic Targets 2018, 22(10), 833-848.

Efthymiou et al., "Evaluation of siRNAs that Contain Internal Variable-Length Spacer Linkages," Bioorganic & Medicinal Chemistry Letters 2012, 22, 5590-5594.

Engelen et al., "DNA-Based Control of Protein Activity," Chemical Communications 2016, 52(18), 3598-3610.

Estey, "Acute Myeloid Leukemia: 2012 Update on Diagnosis, Risk Stratification, and Management," American Journal of Hematology 2012, 87(1), 89-99.

Exiqon, "LNA™ Oligo Tools and Design Guidelines," exiqon.com 2020, in 1 page. www.exiqon.com/oligo-tools.

Extended European Search Report and Opinion dated Apr. 14, 2022 in European Patent Application No. 19846651.8.

Filipi et al., "Glial cells—The strategic targets in amyotrophic lateral sclerosis treatment," Journal of Clinical Medicine 2020, 9(1), in 47 pages.

Final Office Action dated Jul. 21, 2023 in U.S. Appl. No. 17/172,461.

First Office Action dated Feb. 27, 2023 in Chinese Patent Application No. 201880066486.5.

Fleige et al., "Stimuli-responsive polymeric nanocarriers for the controlled transport of active compounds: Concepts and applications," Advanced Drug Delivery Reviews 2012, 64(9), 866-884.

Gawande et al., "Selection of DNA aptamers with two modified bases," Proceedings of the National Academy of Sciences 2017, 114, 2898-2903.

Glaser et al., "Anti-apoptotic Mcl-1 is Essential for the Development and Sustained Growth of Acute Myeloid Leukemia," Genes & Development 2012, 26, 120-125.

Glen Research, "Locked Analog Phosphoramidites and Supports," Glenresearch.com 2023, in 4 pages. https://www.glenresearch.com/products/labels-and-modifiers/backbone-modification/locked-analog-phosphoramidites.html.

Glen Research, "Nucleoside Analog Phosphoramidites," Glenresearch.com 2023, in 3 pages. https://www.glenresearch.com/browse/nucleoside-analog-phosphoramidites.

Glen Research, "Modification and Labeling," glenresearch.com 2023, in 6 pages. www.glenresearch.com/browse/labels-and-modifiers.

Graham et al., "Isolation, Culture, and Functional Characterization of Adult Mouse Cardiomyoctyes," JoVE 2013, 79, in 13 pages.

Green et al., "Complex Cellular Logic Computation Using Ribocomputing Devices," Nature 2017, 548(7665), 117-121.

Green et al., "To kill a microglia: a case for CSF1R inhibitors," Trends in Immunology 2020, 41(9), 771-784.

Groves et al., "Computing in Mammalian Cells with Nucleic Acid Strand Exchange," Nature Nanotechnology 2016, 11(3), 287-294.

GSRS, "Casimersen," nih.gov 2023, in 1 page. https://gsrs.ncats.nih.gov/ginas/app/beta/substances/905e0f05-b9c5-412c-a0e1-5bb898111944.

GSRS, "Eteplirsen," nih.gov 2023, in 1 page. https://gsrs.ncats.nih.gov/ginas/app/beta/substances/4d0cddf7-f088-45af-af78-27659898e442.

GSRS, "Golodirsen," nih.gov 2023, in 1 page. https://gsrs.ncats.nih.gov/ginas/app/beta/substances/e54505d8-4af5-43f6-95b4-f70effe0b457.

Guo, "The Emerging Field of RNA Nanotechnology," Nature Nanotechnology 2010, 5(12), 833-842.

Guttenplan et al., "Knockout of reactive astrocyte activating factors slows disease progression in an ALS mouse model," Nature Communications 2020, 11(1), in 9 pages.

Ha & Kim, "Regulation of MicroRNA Biogenesis," Nature Reviews Molecular Cell Biology 2014, 15, 509-524.

Hammond et al., "Delivery of oligonucleotide-based therapeutics: challenges and opportunities," EMBO Molecular Medicine 2021, 13(4), e13243.

Han et al., "Programmable siRNA Pro-Drugs that Activate RNAi Activity in Response to Specific Cellular RNA Biomarkers," Molecular Therapy—Nucleic Acids 2022, 27, 797-809.

Hartmann et al., "Effects of phenylephrine on calcium current and contractility of feline ventricular myocytes," American Journal of Physiology-Heart and Circulatory Physiology 1988, 255, H1173-H1180.

Heissig et al., "DNA as Tunable Adaptor for siRNA Polyplex Stabilization and Functionalization," Molecular Therapy—Nucleic Acids 2016, 5, in 10 pages.

Hill et al., "Sonic hedgehog signaling in astrocytes," Cellular and Molecular Life Sciences 2021, 78, 1393-1403.

Hochrein et al., "Conditional Dicer Substrate Formation via Shape and Sequence Transduction with Small Conditional RNAs," Journal of the American Chemical Society 2013, 135, 17322-17330.

Hochrein et al., "Signal Transduction in Human Cell Lysate via Dynamic RNA Nanotechnology," ACS Synthetic Biology 2018, 7, 2796-2802.

Hope & Trono, "Structure, Expression, and Regulation of the HIV Genome," HIV In Site 2020, in 11 pages. http://hivinsite.ucsf.edu/InSite?page=kb-OO&doc=kb-02-01-02.

Horizon, "Dharmacon reagents," horizondiscovery.com 2023, in 8 pages. http://dharmacon.horizondiscovery.com/design-center/.

Hu et al., "Therapeutic siRNA: state of the art," Signal Transduction and Targeted Therapy 2020, 5(1), in 25 pages.

Huang et al., "Activation of Wnt/β-catenin signalling via GSK3 inhibitors direct differentiation of human adipose stem cells into functional hepatocytes," Scientific Reports 2017, 7(1), in 12 pages.

Integrated DNA Technologies, "Oligo Modifications," idtdna.com 2023, in 2 pages. https://www.idtdna.com/pages/products/custom-dna-rna/oligo-modifications.

International Search Report and Written Opinion dated Jan. 4, 2019 in PCT Patent Application No. PCT/US2018/046383.

International Search Report and Written Opinion dated Jan. 25, 2023 in PCT Patent Application No. PCT/US2022/078466.

International Search Report and Written Opinion dated Nov. 25, 2019 in PCT Patent Application No. PCT/US2019/046075.

International Search Report and Written Opinion dated Nov. 26, 2018 in PCT Patent Application No. PCT/US2018/046379.

International Search Report and Written Opinion dated Oct. 4, 2022 in PCT Patent Application No. PCT/US2022/073426.

International Search Report and Written Opinion dated Oct. 27, 2022 in PCT Patent Application No. PCT/US2022/073432.

International Search Report and Written Opinion dated Sep. 14, 2022 in PCT Patent Application No. PCT/US2022/073430.

International Search Report and Written Opinion dated Sep. 23, 2022 in PCT Patent Application No. PCT/US2022/073428.

International Search Report and Written Opinion dated Sep. 28, 2022 in PCT Patent Application No. PCT/US2022/073431.

International Search Report and Written Opinion dated Sep. 20, 2018 in PCT Patent Application No. PCT/US2018/042195.

International Search Report and Written Opinion dated Sep. 28, 2022 in PCT Patent Application No. PCT/US2022/073433.

Iwamoto et al., "Control of Phosphorothioate Stereochemistry Substantially Increases the Efficacy of Antisense Oligonucleotides," Nature Biotechnology 2017, 35(9), 845-851.

Jafar-Nejad et al., "The atlas of RNase H antisense oligonucleotide distribution and activity in the CNS of rodents and non-human primates following central administration," Nucleic Acids Research 2021, 49(2), 657-673.

Japanese Office Action dated Jul. 4, 2023 in Japanese Patent Application No. 2021531622.

Japanese Search Report dated Jun. 23, 2023 in Japanese Patent Application No. 2021531622.

Jaramillo-Botero et al., "First-principles-based multiscale, multiparadigm molecular mechanics and dynamics methods for describing complex chemical processes," Multiscale Molecular Methods in Applied Chemistry 2012, 1-42.

Jessup & Brozena, "Heart Failure," New England Journal of Medicine 2003, 348, 2007-2018.

(56) References Cited

OTHER PUBLICATIONS

Joe et al., "Astrocytes, microglia, and Parkinson's disease," Experimental Neurobiology 2018, 27(2), 77-87.

Kadkol et al., "Comprehensive Analysis of CBFbeta-MYH11 Fusion Transcripts in Acute Myeloid Leukemia by RT-PCR Analysis," The Journal of Molecular Diagnostics 2004, 6(1), 22-27.

Katanosaka et al., "Calcineurin Inhibits Na+/Ca2+ Exchange in Phenylephrine-treated Hypertrophic Cardiomyocytes," Journal of Biological Chemistry 2005, 280, 5764-5772.

Keum et al., "Design, assembly, and activity of antisense DNA nanostructures," Small 2011, 7(24), 3529-3535.

Khvorova & Watts, "The chemical evolution of oligonucleotide therapies of clinical utility," Nature Biotechnology 2017, 35, 238-248.

Kim et al., "Synthetic dsRNA Dicer Substrates Enhance RNAi Potency and Efficacy," Nature Biotechnology 2005, 23(2), 222-226.

Knerr et al. "Glucagon like peptide 1 receptor agonists for targeted delivery of antisense oligonucleotides to pancreatic beta cell," Journal of the American Chemical Society 2021, 143(9), 3416-3429.

Konstam et al., "Left ventricular remodeling in heart failure: current concepts in clinical significance and assessment," JACC Cardiovasc Imaging 2011, 4(1), 98-108.

Kumar et al., "Combinatorially Inducible RNA Interference Triggered by Chemically Modified Oligonucleotides," Journal of the American Chemical Society 2011, 133, 2783-2788.

Kundu & Liu, "Function of the inv(16) Fusion Gene CBFB-MYH11," Hematology 2001, 8, 201-205.

Landry et al., "Progress in RNAi-Mediated Molecular Therapy of Acute and Chronic Myeloid Leukemia," Molecular Therapy—Nucleic Acids 2015, 4, in 23 pages.

Lee et al., "Differential Roles of Human Dicer-Binding Proteins TRBP and PACT in Small RNA Processing," Nucleic Acids Research 2013, 41(13), 6568-6576.

Lee et al., "Molecularly self-assembled nucleic acid nanoparticles for targeted in vivo siRNA delivery," Nature Nanotechnology 2012, 7, 389-393.

Lennox et al., "Improved Performance of Anti-miRNA Oligonucleotides Using a Novel Non-Nucleotide Modifier," Molecular Therapy—Nucleic Acids 2013, 2, in 19 pages.

Li et al., "Antiparallel DNA Double Crossover Molecules as Components for Nanoconstruction," Journal of the American Chemical Society 1996, 118, 6131-6140.

Lind et al., "Parameterization and Simulation of the Physical Properties of Phosphorothioate Nucleic Acids," Journal of the American Chemical Society 1998, 3, 41-54.

Liu et al., "miR-222 Is Necessary for Exercise-Induced Cardiac Growth and Protects against Pathological Cardiac Remodeling," Cell Metabolism 2015, 21, 584-595.

Loakes, "Survey and summary: The applications of universal DNA base analogues," Nucleic Acids Research 2001, 29(12), 2437-2447.

Look, "Oncogenic Transcription Factors in the Human Acute Leukemias," Science 1997, 278, 1059-1064.

Lu et al., "Linkers having a crucial role in antibody-drug conjugates," International Journal of Molecular Sciences 2016, 17, 561.

Lutgen et al., "β-Catenin signaling positively regulates glutamate uptake and metabolism in astrocytes," Journal of Neuroinflammation 2016, 13, 1-13.

Macke & Case, "Modeling Unusual Nucleic Acid Structures," ACS Symposium Series, American Chemical Society 1998, 24, 379-393.

Macrae et al., "Structural Basis for Double-Stranded RNA Processing by Dicer," Science 2006, 311, 195-198.

Mark & Nilsson, "Structure and Dynamics of the TIP3P, SPC, and SPC/E Water Models at298 K.," The Journal of Physical Chemistry A 2001, 105, 9954-9960.

Marks et al., "Histone deacetylases and cancer: causes and therapies," Nature Reviews Cancer 2001, 1(3), 194.

Mathews et al., "Expanded Sequence Dependence of Thermodynamic Parameters Improves Prediction of RNA Secondary Structure," Journal of Molecular Biology 1999, 288, 911-940.

Mathews Lab, "RNAstructure, Version 6.4," rochester.edu 2023, in 1 page. http://rna.urmc.rochester.edu/RNAstructure.html.

Mathy et al., "5'-to-3' Exoribonuclease Activity in Bacteria: Role of Rnase J1 in rRNA Maturation and 5' Stability of mRNA," Cell 2007, 129, 681-692.

Matsukura et al., "Phosphorothioate Analogs of Oligodeoxynucleotides: Inhibitors of Replication and Cytopathic Effects of Human Immunodeficiency Virus," Proceedings of the National Academy of Sciences 1987, 84, 7706-7710.

Meggers et al., "Synthesis and Properties of the Simplified Nucleic Acid Glycol Nucleic Acid," Accounts of Chemical Research 2010, 43(8), 1092-1102.

Millipore Sigma, "Locked Nucleic Acid," sigmaaldrich.com 2023, in 5 pages. www.sigmaaldrich.com/technical-documents/articles/biology/locked-nucleic-acids-faq.html.

Mirbase, "Stem-loop sequence hsa-mir-23a," mirbase.org 2023, in 3 pages. https://www.mirbase.org/cgi-bin/mirna_entry.pl?acc=MI0000079.

Molkentin et al., "Calcineurin-Dependent Transcriptional Pathway for Cardiac Hypertrophy," Cell 1998, 93, 215-228.

Morel et al., "Neuronal exosomal miRNA-dependent translational regulation of astroglial glutamate transporter GLT1," Journal of Biological Chemistry 2013, 288(10), 7105-7116.

Mukherjee et al., "Design of a DNA-Programmed Plasminogen Activator," Journal of the American Chemical Society 2018, 140(45), 15516-15524.

Naito & Kumiko, "Designing functional siRNA with reduced off-target effects," siRNA Design: Methods and Protocols 2013, 57-68.

Nearest Neighbor Database, "Introduction and Definitions," rochester.edu 2023, in 4 pages. https://rna.urmc.rochester.edu/NNDB/help.html.

Nearest Neighbor Database, "Version 1.02, Released Apr. 4, 2011," rochester.edu 2023, in 3 pages. https://rna.urmc.rochester.edu/NNDB/index.html.

Nolan et al., "Quantification of mRNA using real-time RT-PCR," Nature Protocols 2006, 1(3), 1559-1582.

Non-Final Office Action dated Dec. 24, 2021 in U.S. Appl. No. 16/786,793.

Non-Final Office Action dated Jan. 24, 2023 in U.S. Appl. No. 17/172,461.

Non-Final Office Action dated Jun. 23, 2022 in U.S. Appl. No. 16/786,793.

Notice of Allowance dated Jan. 12, 2023 in U.S. Appl. No. 16/786,793.

Opferman et al., "Obligate Role of Anti-Apoptotic MCL-1 in the Survival of Hematopoietic Stem Cells," Science 2005, 307(5712), 1101-1104.

Orban & Izaurralde, "Decay of mRNAs Targeted by RISC Requires XRN1, the Ski Complex, and the Exosome," RNA 2005, 11, 459-469.

Owczarzy et al., "IDT SciTools: a suite for analysis and design of nucleic acid oligomers," Nucleic Acids Research 2008, 36(suppl_2), W163-W169.

Pajarillo et al., "Astrocyte-specific deletion of the transcription factor Yin Yang 1 in murine substantia nigra mitigates manganese-induced dopaminergic neurotoxicity," Journal of Biological Chemistry 2020, 295(46), 15662-15676.

Paradis et al., "Newborn Hypoxia/Anoxia Inhibits Cardiomyocyte Proliferation and Decreases Cardiomyocyte Endowment in the Developing Heart: Role of Endothelin-1," Plos One 2015, 10, in 21 pages.

Pettersen et al., "UCSF Chimera—A Visualization System for Exploratory Research and Analysis," Journal of Computational Chemistry 2004, 25, 1605-1612.

Pi et al., "RNA nanoparticles harboring annexin A2 aptamer can target ovarian cancer for tumor-specific doxorubicin delivery," Nanomedicine 2017, 13(3), 1183-1193.

Picco & Garnett, "A Road Map for Precision Cancer Medicine Using Personalized Models," Cancer Discovery 2017, 7(5), 456-458.

Plimpton, "Fast Parallel Algorithms for Short-Range Molecular Dynamics," Journal of Computational Physics 1995, 117, 1-19.

(56) References Cited

OTHER PUBLICATIONS

Qi et al., "HDAC8 Inhibition Specifically Targets Inv(16) Acute Myeloid Leukemic Stem Cells by Restoring p53 Acetylation," Cell Stem Cell 2015, 17(5), 597-610.

Qiagen, "Design Guidelines," qiagen.com 2020, in 1 page. https://www.qiagen.com/us/service-and-support/learning-hub/technologies-and-research-topics/lna/custom-lna-design-and-applications/lna-design-tools-calculators/lna-oligo-tm-prediction/.

Qiagen, "LNA Oligo Optimizer," qiagen.com 2020, in 1 page. https://www.qiagen.com/us/service-and-support/learning-hub/technologies-and-research-topics/lna/custom-lna-design-and-applications/lna-design-tools-calculators/lna-oligo-optimizer/.

Red Server, "RESP ESP charge Derive server," q4md-forcefieldtools.org 2023, in 2 pages. q4md-forcefieldtools.org/REDServer/.

Restriction Requirement dated Apr. 30, 2021 in U.S. Appl. No. 16/786,793.

Restriction Requirement dated Aug. 3, 2023 in U.S. Appl. No. 16/631,134.

Restriction Requirement dated Aug. 19, 2022 in U.S. Appl. No. 17/172,461.

Restriction Requirement dated May 23, 2023 in U.S. Appl. No. 16/638,107.

Rij, "Virus meets RNAi. Symposium on Antiviral Applications of RNA Interference," EMBO Reports 2008, 9(8), 725-729.

Robinson et al., "Integrative clinical genomics of metastatic cancer," Nature 2017, 548(7667), 297-303.

Rojo et al., "GSK-3β down-regulates the transcription factor Nrf2 after oxidant damage: relevance to exposure of neuronal cells to oxidative stress," Journal of Neurochemistry 2008, 105(1), 192-202.

Rothemund, "Folding DNA to create nanoscale shapes and patterns," Nature 2006, 440 (7082), 297-302.

Sabir et al., "Branchpoint expansion in a fully complementary three-way DNA junction," Journal of the American Chemical Society 2012, 134(14), 6280-6285.

Sano et al., "Effect of asymmetric terminal structures of short RNA duplexes on the RNA interference activity and strand selection," Nucleic Acids Research 2008, 36, 5812-5821.

Scherer et al., "Optimization and Characterization of tRNA-shRNA Expression Constructs," Nucleic Acids Research 2007, 35(8), 2620-2628.

Schlegel et al., "Chirality Dependent Potency Enhancement and Structural Impact of Glycol Nucleic Acid Modification on siRNA," Journal of the American Chemical Society 2017, 139, 8537-8546.

Second Office Action dated Sep. 20, 2023 in Chinese Patent Application No. 201880066486.5.

Seeman, "DNA in a Material World," Nature 2003, 421, 427-431.

Setten et al., "The Current State and Future Directions of RNAi-Based Therapeutics," Nature Reviews Drug Discovery 2019, 18, 421-446.

Shu et al., "Programmable folding of fusion RNA in vivo and in vitro driven by pRNA 3WJ motif of phi29 DNA packaging motor," Nucleic Acids Research 2014, 42(2), in 9 pages.

Shu et al., "Thermodynamically stable RNA three-way junction for constructing multifunctional nanoparticles for delivery of therapeutics," Nature Nanotechnology 2011, 6, 658-667.

Shukla et al., "Exploring Chemical Modifications for siRNA Therapeutics: A Structural and Functional Outlook," ChemMedChem 2010, 5, 328-349.

Silverman, "Control of Macromolecular Structure and Function Using Covalently Attached Double-Stranded DNA Constraints," Molecular BioSystems 2007, 3, 24-29.

Srinivas et al., "On the Biophysics and Kinetics of Toehold-Mediated DNA Strand Displacement," Nucleic Acids Research 2013, 41(22), 10641-10658.

Srinivasan et al., "Alzheimer's patient microglia exhibit enhanced aging and unique transcriptional activation," Cell Reports 2020, 31(13), in 20 pages.

Supplementary European Search Report and European Search Opinion dated Apr. 8, 2021 in European Patent Application No. 18844244.6.

Sussman et al., "Prevention of Cardiac Hypertrophy in Mice by Calcineurin Inhibition," Science 1998, 281, 1690-1693.

Tham et al., "Pathophysiology of cardiac hypertrophy and heart failure: signaling pathways and novel therapeutic targets," Archives of Toxicology 2015, 89, 1401-1438.

The Nupack Team, "Nupack Cloud Alpha," nupack.org 2023, in 1 page. http://nupack.org.

Theoretical Biochemistry Group, "The ViennaRNA Package," Universitat Wien 2023, in 7 pages. https://www.tbi.univie.ac.at/RNA/.

Tolstrup et al., "OligoDesign: Optimal Design of LNA (Locked Nucleic Acid) Oligonucleotide Capture Probes for Gene Expression Profiling," Nucleic Acids Research 2003, 31 (13), 3758-3762.

Trivedi et al., "Hdac2 regulates the cardiac hypertrophic response by modulating Gsk3J3 activity," Nature Medicine 2007, 13, 324-331.

Turner & Mathews, "NNDB: the nearest neighbor parameter database for predicting stability of nucleic acid secondary structure," Nucleic Acids Research 2010, 38(suppl_1), D280-D282.

Vargas & Johnson, "The Nrf2-ARE cytoprotective pathway in astrocytes," Expert Reviews in Molecular Medicine 2009, 11, in 20 pages.

Verma & Eckstein, "Modified oligonucleotides: synthesis and strategy for users," Annual Review of Biochemistry 1998, 67(1), 99-134.

Walsh et al., "DNA cage delivery to mammalian cells," ACS Nano 2011, 5(7), 5427-5432.

Wang et al., "Development and Testing of a General Amber Force Field," Journal of Computational Chemistry 2004, 25, 1157-1174.

Wikipedia, "Locked Nucleic Acid," eikipedia.org 2023, in 4 pages. https://en.wikipedia.org/wiki/Locked_nucleic_acid.

Wolfe et al., "Constrained multistate sequence design for nucleic acid reaction pathway engineering," Journal of the American Chemical Society 2017, 139, 3134-3144.

Wolfe et al., "Sequence design for a test tube of interacting nucleic acid strands," ACS Synthetic Biology 2015, 4, 1086-1100.

X3DNA, "x3DNA-DSSR: The Next Generation of 3DNA with Unmatched Features for RNA Structural Bioinformatics," x3dna.org 2023, in 3 pages. https://x3dna.org/articles/seeing-is-understanding-as-well-as-believing.

Xiao et al., "miR-31a-5p promotes postnatal cardiomyocyte proliferation by targeting RhoBTB1," Experimental & Molecular Medicine 2017, 49, in 10 pages.

Yang et al., "Studies of the 5' Exonuclease and Endonuclease Activities of CPSF-73 in Histone Pre-mRNA Processing," Molecular and Cellular Biology 2009, 29(1), 31-42.

Yurke et al., "A DNA-Fuelled Molecular Machine Made of DNA," Nature 2000, 406, 605-608.

Zadeh et al., "Nucleic acid sequence design via efficient ensemble defect optimization," Journal of Computational Chemistry 2011, 32, 439-452.

Zadeh et al., "NUPACK: analysis and design of nucleic acid systems," Journal of Computational Chemistry 2011, 32, 170-173.

Zhang et al., "Mcl-1 is Critical for Survival in a Subgroup of Non-Small-Cell Lung Cancer Cell Lines," Oncogene 2011, 30, 1963-1968.

Zhang et al., "Structural DNA nanotechnology: state of the art and future perspective," Journal of the American Chemical Society 2014, 136(32), 11198-111211.

Zhou et al., "Selection, Characterization and Application of New RNA HIV gp 120 Aptamers for Facile Delivery of Dicer Substrate siRNAs into HIV Infected Cells," Nucleic Acids Research 2009, 37(9), 3094-3109.

Advisory action dated Sep. 5, 2024 in U.S. Appl. No. 16/638,107.

Dai, Yifan et al. "Strand displacement strategies for biosensor applications." Trends in biotechnology 37.12 (2019): 1367-1382.

De Windt, Leon J., et al. "Targeted inhibition of calcineurin attenuates cardiac hypertrophy in vivo." Proceedings of the National Academy of Sciences 98.6 (2001): 3322-3327.

(56)　　　　　References Cited

OTHER PUBLICATIONS

Fiedler et al., "Quantitative RT-PCR Methods for Mature microRNA Expression Analysis," RT-PCR Protocols: Second Edition 2010, 49-64.

Final Office Action dated Jul. 3, 2024 in U.S Appl. No. 16/638,107.

Fornace, Mark E., et al. "NUPACK: analysis and design of nucleic acid structures, devices, and systems." (2022).

Genebank "*Homo sapiens* glycogen synthase kinase 3 beta (GSK3B), transcript variant 1, mRNA", available at: "https://www.ncbi.nlm.nih.gov/nuccore/NM_002093.4" last accessed on Jun. 7, 2024 printed in 5 Pages.

Genebank "*Homo sapiens* glycogen synthase kinase 3 beta (GSK3B), transcript variant 2, mRNA", available at: "https://www.ncbi.nlm.nih.gov/nuccore/NM_001146156.2" last accessed on Jun. 7, 2024 printed in 6 Pages.

Genebank "*Homo sapiens* glycogen synthase kinase 3 beta (GSK3B), transcript variant 3, mRNA", available at: "https://www.ncbi.nlm.nih.gov/nuccore/NM_001354596.2" last accessed on Jun. 7, 2024 printed in 5 Pages.

Genebank "*Homo sapiens* inhibitor of nuclear factor kappa B kinase subunit beta (IKBKB), transcript variant 1, mRNA", available at: "https://www.ncbi.nlm.nih.gov/nuccore/NM_001556.3" last accessed on Jun. 12, 2024 printed in 8 Pages.

Genebank "*Homo sapiens* inhibitor of nuclear factor kappa B kinase subunit beta (IKBKB), transcript variant 2, mRNA", available at: "https://www.ncbi.nlm.nih.gov/nuccore/1831772119" last accessed on Jun. 12, 2024 printed in 6 Pages.

Genebank "*Homo sapiens* inhibitor of nuclear factor kappa B kinase subunit beta (IKBKB), transcript variant 7, mRNA", available at: "https://www.ncbi.nlm.nih.gov/nuccore/1677531062" last accessed on Jun. 12, 2024 printed in 6 Pages.

Genebank "*Homo sapiens* RELA proto-oncogene, NF-kB subunit (RELA), transcript variant 1, mRNA", available at: "https://www.ncbi.nlm.nih.gov/nuccore/NM_021975.4" last accessed on Jun. 12, 2024 printed in 6 Pages.

Genebank "*Homo sapiens* RELA proto-oncogene, NF-kB subunit (RELA), transcript variant 2, mRNA", available at: "https://www.ncbi.nlm.nih.gov/nuccore/NM_001145138.2" last accessed on Jun. 12, 2024 printed in 6 Pages.

Genebank "*Homo sapiens* RELA proto-oncogene, NF-kB subunit (RELA), transcript variant 3, mRNA", available at: "https://www.ncbi.nlm.nih.gov/nuccore/NM_001243984.2" last accessed on Jun. 12, 2024 printed in 4 Pages.

Genebank "*Homo sapiens* RELA proto-oncogene, NF-kB subunit (RELA), transcript variant 4, mRNA", available at: "https://www.ncbi.nlm.nih.gov/nuccore/NM_001243985.2" last accessed on Jun. 12, 2024 printed in 4 Pages.

Genebank "Mus musculus glycogen synthase kinase 3 beta (Gsk3b), transcript variant 1, mRNA", available at: "https://www.ncbi.nlm.nih.gov/nuccore/1365045870" last accessed on Jun. 12, 2024 printed in 6 Pages.

Genebank "Mus musculus glycogen synthase kinase 3 beta (Gsk3b), transcript variant 2, mRNA", available at: "https://www.ncbi.nlm.nih.gov/nuccore/NM_001347232.1" last accessed on Jun. 7, 2024 printed in 6 Pages.

Genebank "Mus musculus inhibitor of kappaB kinase beta (Ikbkb), transcript variant 1, mRNA", available at: "https://www.ncbi.nlm.nih.gov/nuccore/NM_001159774.1" last accessed on Jun. 12, 2024 printed in 7 Pages.

Genebank "Mus musculus inhibitor of kappaB kinase beta (Ikbkb), transcript variant 2, mRNA" available at: "https://www.ncbi.nlm.nih.gov/nuccore/NM_010546.2" last accessed on Jun. 12, 2024 printed in 7 Pages.

Genebank "Mus musculus v-rel reticuloendotheliosis viral onco-gene homolog A (avian) (Rela), transcript variant 1, mRNA", available at: "https://www.ncbi.nlm.nih.gov/nuccore/NM_009045.5" last accessed on Jun. 12, 2024 printed in 6 Pages.

Genebank "Mus musculus v-rel reticuloendotheliosis viral onco-gene homolog A (avian) (Rela), transcript variant 2, mRNA", available at: "https://www.ncbi.nlm.nih.gov/nuccore/NM_001365067.1" last accessed on Jun. 12, 2024 printed in 6 Pages.

Genebank "Predicted: Mus musculus glycogen synthase kinase 3 beta (Gsk3b), transcript variant X1, mRNA", available at: "https://www.ncbi.nlm.nih.gov/nuccore/XM_030249221.2" last accessed on Jun. 12, 2024 printed in 3 Pages.

Genecards: The Human Gene Database. Myosin Heavy Chain 7 (MYH7), available at: "www.genecards.org/cgi-bin/carddisp.pl?gene=MYH7", last accessed on Apr. 12, 2024 printed in 34 pages.

Gethers, Matthew Leroy. Therapeutic Opportunities and Approaches to Sequence Control for Nucleic Acids. California Institute of Technology, 2018.

Holohan et al., "Cancer drug resistance: an evolving paradigm," Nat Rev Cancer 2013, 13(10), 714-26.

Huang, Yong, et al. "Biological functions of microRNAs: a review." Journal of physiology and biochemistry 67 (2011): 129-139.

National Library of Medicine. National Center for Biotechnology Information. Reference Sequence: NM_001527.3. *Homo sapiens* histone deacetylase 2 (HDAC2), transcript variant 1, mRNA. Available at: "www.ncbi.nlm.nih.gov/nuccore/NM_001527.3", last accessed on Apr. 12, 2024 printed in 7 pages.

Non-Final Office Action dated Feb. 3, 2025 in U.S. Appl. No. 16/638,107.

Non-Final Office Action dated Jan. 30, 2024 in U.S. Appl. No. 16/631,134.

Non-Final office action dated Jan. 8, 2024 in U.S. Appl. No. 16/638,107.

Notice of Allowance from U.S. Appl. No. 17/172,461 dated Feb. 9, 2024.

Notice of Allowance from U.S. Appl. No. 16/631,134 dated Jun. 5, 2024.

Office Action dated Jan. 9, 2024 in Japanese Patent Application No. 2021-531622.

Office Action dated Sep. 26, 2024 in Chinese Patent Application No. 201980067384.X.

Office Action dated Nov. 11, 2023 in Chinese Patent Application No. 201980067384.X.

Qiagen. LNA Oligo Tm Prediction. Available at: "qiagen.com/us/service-and-suppor/learning-hub/technologies-and-research-topics/lna/custom-lna-design-and-applications/lna-design-tools-calculators/lna-oligo-tm-prediction/", Last accessed on Sep. 25, 2023 printed in 2 Pages.

RESP ESP charge Derive (RED) Server Development. Available at: "https://upjv.q4md-forcefieldtools.org/REDServer-Development/" last accessed on Apr. 12, 2024, printed in 2 pages.

SFOLD—Software for Statistical Folding and Studies of Regulatory RNAs, available at "https://sfold.wadsworth.org/cgi-bin/index.pl" last accessed on Jan. 17, 2014, printed in 3 pages.

Simmel, Friedrich C. et al., "Principles and applications of nucleic acid strand displacement reactions." Chemical reviews 119.10 (2019): 6326-6369.

The Human Protein Atlas available at:"https://www.proteinatlas.org/" last accessed on Jun. 7, 2024 printed in 1 Page.

Thermo Fisher Scientific Inc. Ppp3ca (protein phosphatase 3, catalytic subunit, alpha isoform) SiRNA ID s72075, available at: "https://www.thermofisher.com/order/genome-database/browse/sirna/keyword/s72075" Last accessed on Apr. 12, 2024 printed in 2 pages.

Thole, Theresa M., et al. "Neuroblastoma cells depend on HDAC11 for mitotic cell cycle progression and survival." Cell death & disease 8.3 (2017): e2635-e2635.

UNAFold, available at: "http://www.unafold.org/", last accessed on Jan. 17, 2024 printed in 1 page.

Wang, Dong, et al. "Atrial natriuretic peptide affects cardiac remodeling, function, heart failure, and survival in a mouse model of dilated cardiomyopathy." Hypertension 63.3 (2014): 514-519.

Zhao et al., "Conditional RNA Interference in gene therapy research progress," Journal of Huazhong University of Science and Technology 2014, 43(4), 478-481.

Fig. 2A

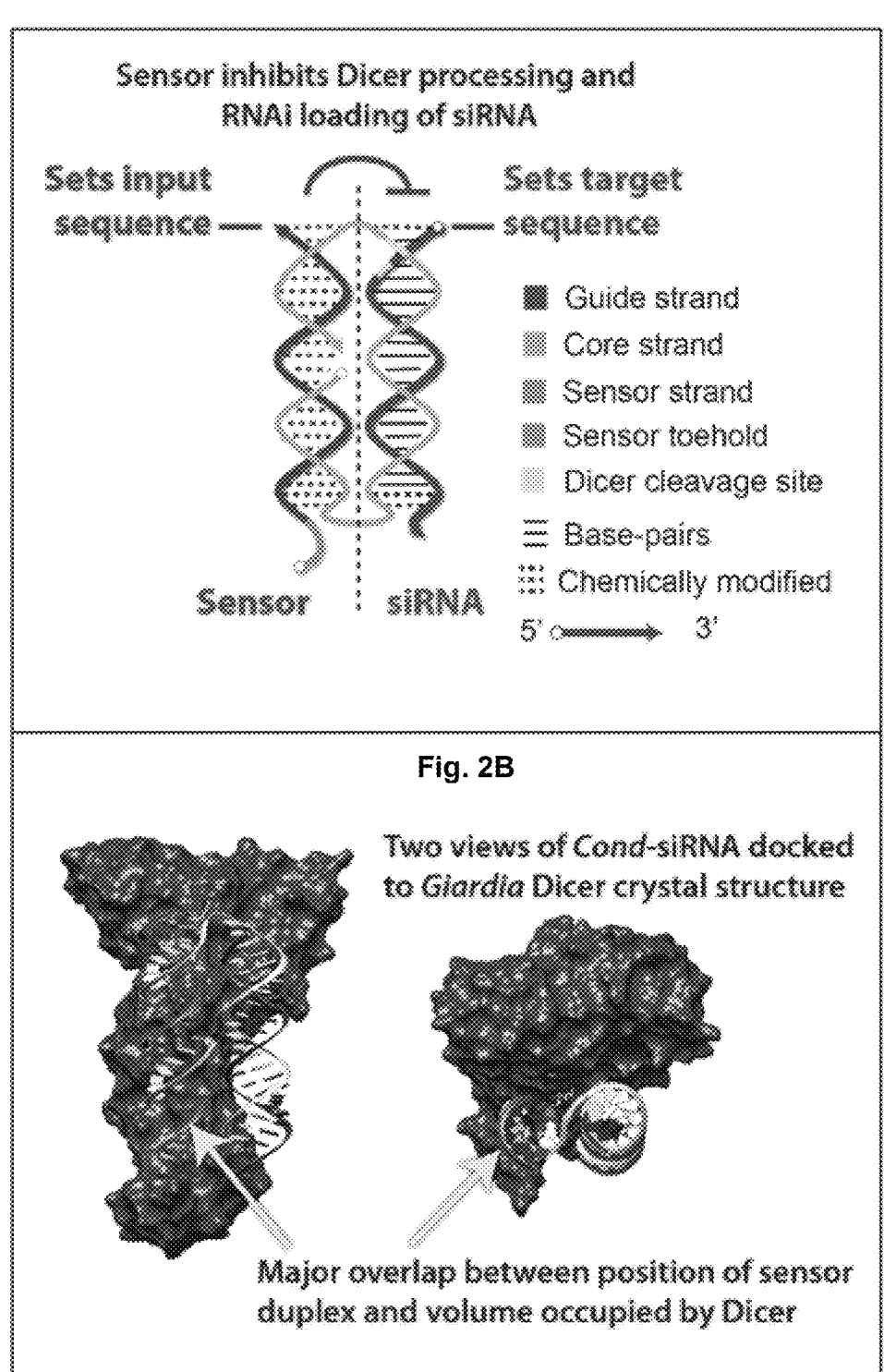

Sensor inhibits Dicer processing and
RNAi loading of siRNA

Sets input
sequence —

Sets target
sequence

- Guide strand
- Core strand
- Sensor strand
- Sensor toehold
- Dicer cleavage site
- Base-pairs
- Chemically modified

5' ⟶ 3'

Sensor        siRNA

Fig. 2B

Two views of *Cond*-siRNA docked
to *Giardia* Dicer crystal structure

Major overlap between position of sensor
duplex and volume occupied by Dicer

Fig. 6

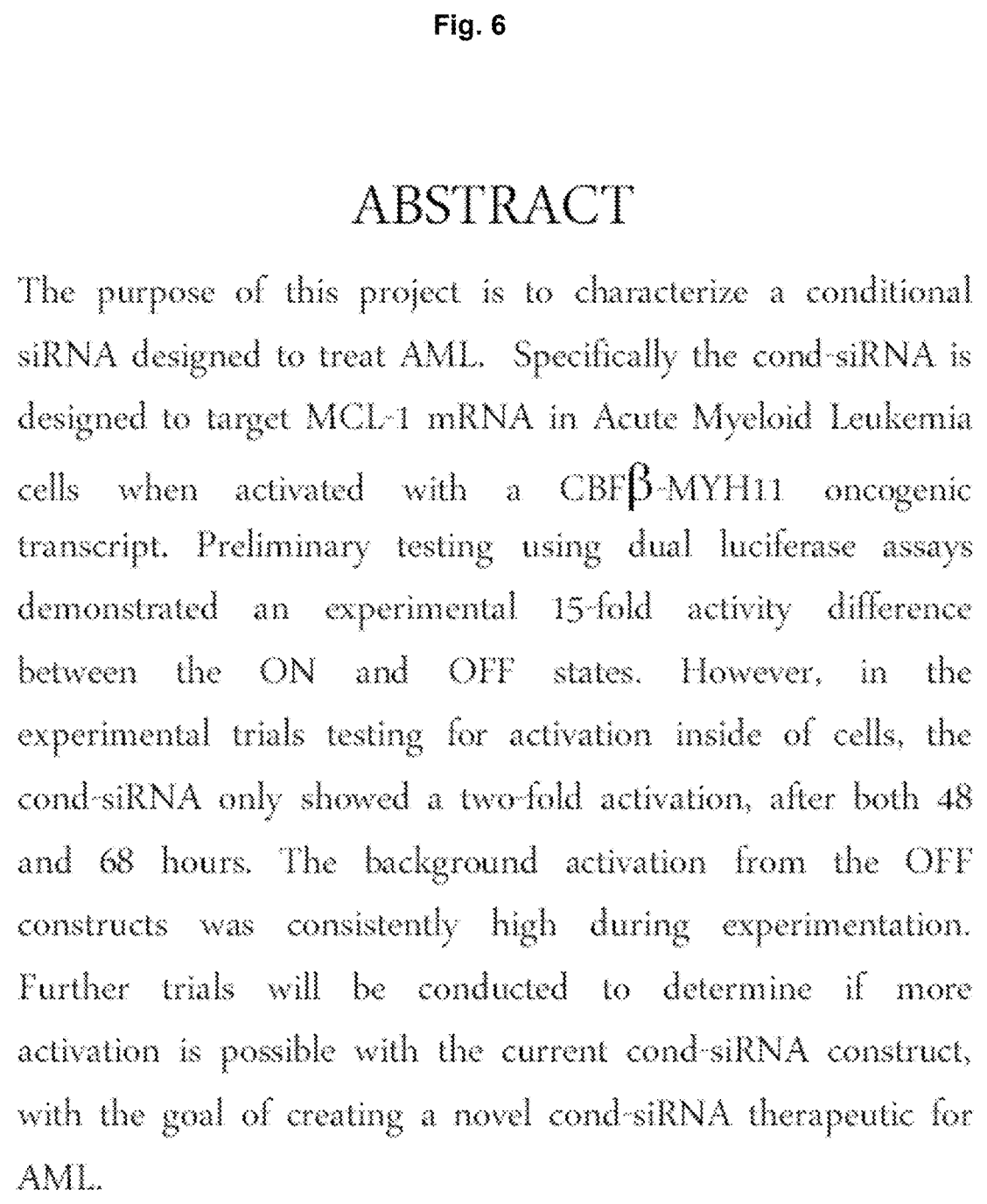

ABSTRACT

The purpose of this project is to characterize a conditional siRNA designed to treat AML. Specifically the cond-siRNA is designed to target MCL-1 mRNA in Acute Myeloid Leukemia cells when activated with a CBFβ-MYH11 oncogenic transcript. Preliminary testing using dual luciferase assays demonstrated an experimental 15-fold activity difference between the ON and OFF states. However, in the experimental trials testing for activation inside of cells, the cond-siRNA only showed a two-fold activation, after both 48 and 68 hours. The background activation from the OFF constructs was consistently high during experimentation. Further trials will be conducted to determine if more activation is possible with the current cond-siRNA construct, with the goal of creating a novel cond-siRNA therapeutic for AML.

Figure 1. (above) conditional siRNA construct.

Figure 2. (below) siRNA conventional vs. improved conditional siRNA. Photos courtesy of Dr. Han

Fig. 9

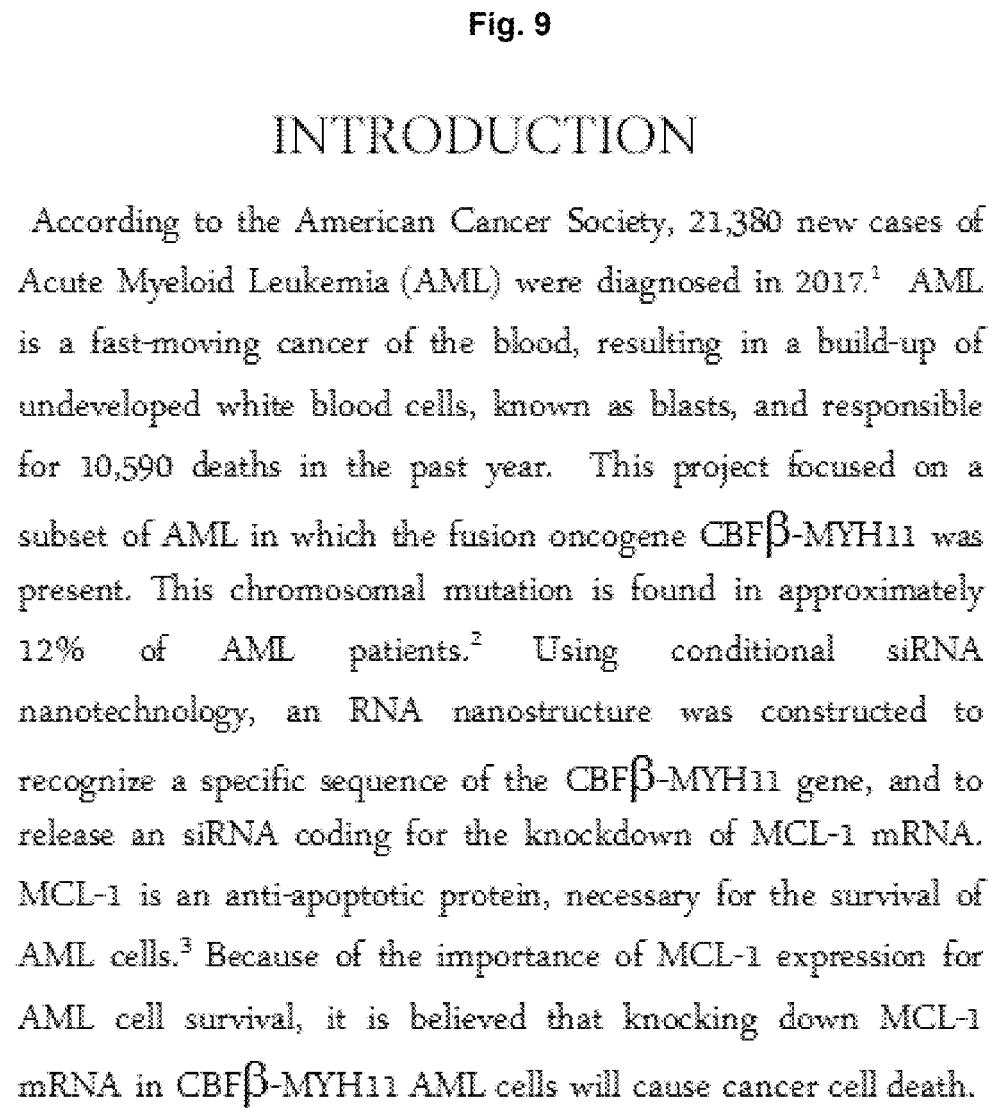

INTRODUCTION

According to the American Cancer Society, 21,380 new cases of Acute Myeloid Leukemia (AML) were diagnosed in 2017.[1] AML is a fast-moving cancer of the blood, resulting in a build-up of undeveloped white blood cells, known as blasts, and responsible for 10,590 deaths in the past year. This project focused on a subset of AML in which the fusion oncogene CBF$\beta$-MYH11 was present. This chromosomal mutation is found in approximately 12% of AML patients.[2] Using conditional siRNA nanotechnology, an RNA nanostructure was constructed to recognize a specific sequence of the CBF$\beta$-MYH11 gene, and to release an siRNA coding for the knockdown of MCL-1 mRNA. MCL-1 is an anti-apoptotic protein, necessary for the survival of AML cells.[3] Because of the importance of MCL-1 expression for AML cell survival, it is believed that knocking down MCL-1 mRNA in CBF$\beta$-MYH11 AML cells will cause cancer cell death.

*Figure 3. (above) sensor strand binding and siRNA activation.*

*Figure 4. (below) RNA interference pathway showing Dicer processing of siRNA, RISC (RNA Induced Silencing Complex) loading, and final Argonaute complex formation.   Photos courtesy of Dr. Han*

*Figure 5. Chromosome 16 inversion that creates the fusion oncogene*

*CBFβ-MYH11.*

*http://atlasgeneticsoncology.org/Anomalies/inv16p13q22TreatRelID1297.html*

Fig. 13

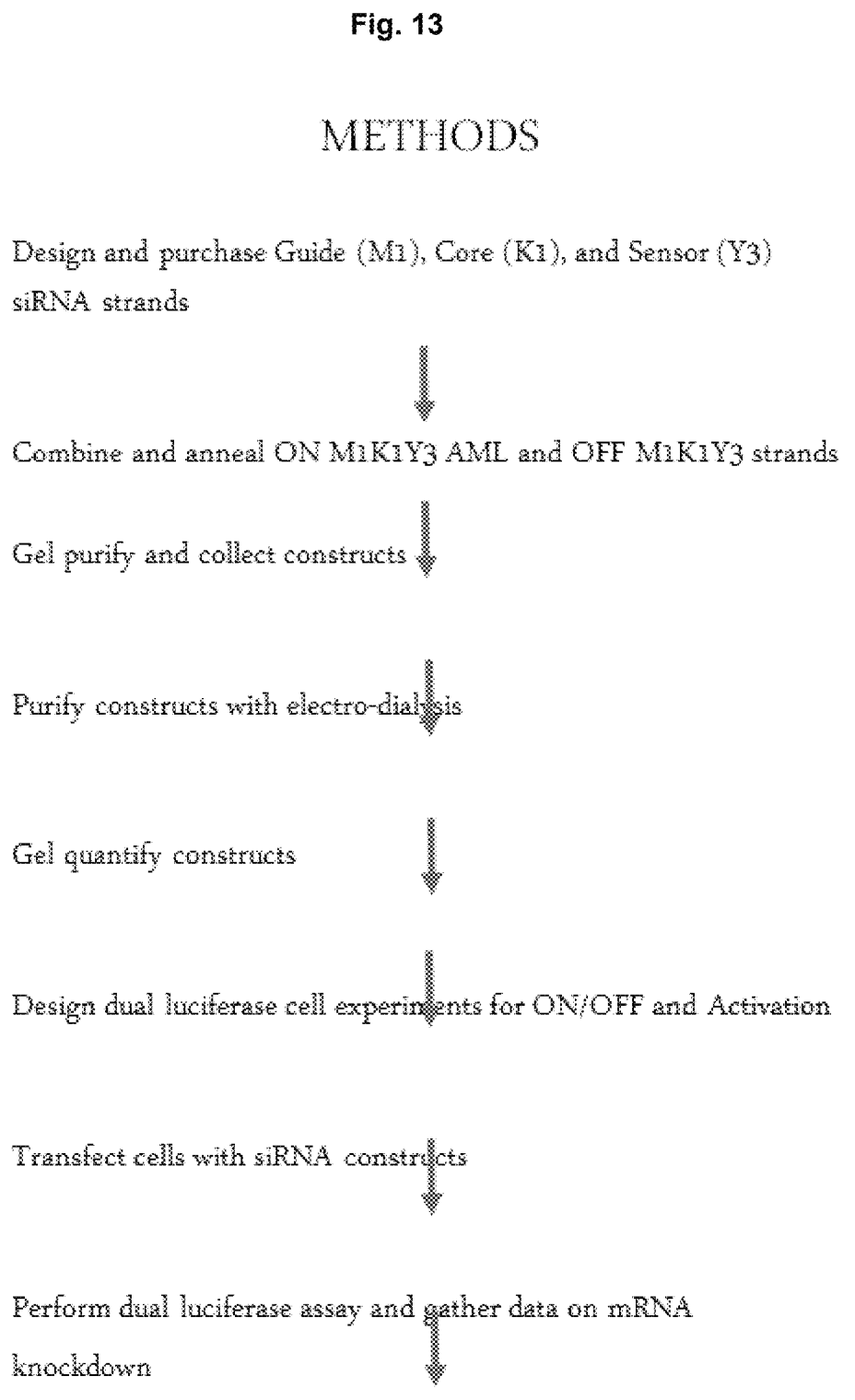

METHODS

Design and purchase Guide (M1), Core (K1), and Sensor (Y3)
siRNA strands

Combine and anneal ON M1K1Y3 AML and OFF M1K1Y3 strands

Gel purify and collect constructs

Purify constructs with electro-dialysis

Gel quantify constructs

Design dual luciferase cell experiments for ON/OFF and Activation

Transfect cells with siRNA constructs

Perform dual luciferase assay and gather data on mRNA
knockdown

Fig. 14

*Figure 6. Quantification of purified cond-siRNA constructs.*

*Lane 1: 100 nm crude cond-siRNA*

*Lane 2: unknown concentration pure cond-siRNA*

*Lane 3: unknown concentration pure cond-siRNA*

*Lane 4: 100 nm crude cond-siRNA*

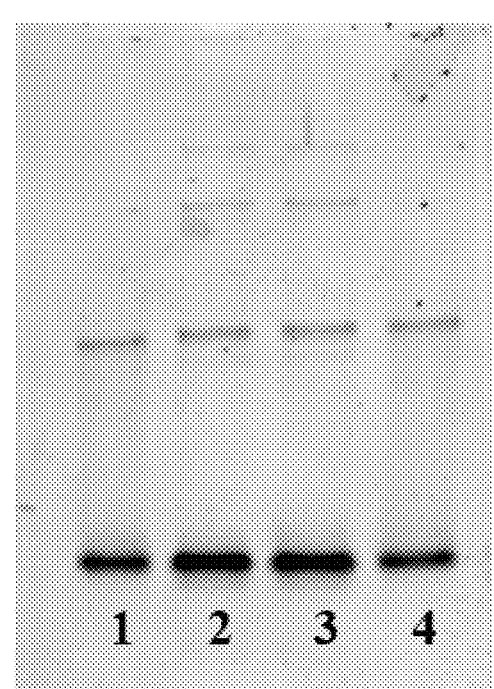

*The Pure was calculated to be at a concentration of 181.2 nM. The fainter bands seen in the gel are representative of impurities, such as strands that did not anneal in the 4 strand ideal siRNA construct.*

Figure 7. Graph of relative renilla fluorescence readout in a dual luciferase assay. HCT116 cells were treated with the M1K1Y3 OFF and M1K1Y3 AML ON siRNA constructs. The OFF construct shows less MCL-1 knockdown than the ON construct. At 1 nM concentration, the OFF construct knocked down about 82% of renilla, while the ON knocked down about 99%.

Figure 8. Graph of first activation experiment of AML cond-siRNA (48 hr). There is around two-fold activation. The 0.06 nM construct in the irr. activator and the AML activator are lower than expected.

| | ON | No activator | Irrelevant activator | AML activator |
|---|---|---|---|---|
| 1.00 nM | 0.8% | 12.0% | 10.3% | 6.3% |
| 0.40 nM | 2.4% | 23.9% | 22.5% | 14.5% |
| 0.16 nM | 6.9% | 47.4% | 41.2% | 29.7% |
| 0.06 nM | 16.1% | 68.6% | 59.8% | 52.4% |

*Figure 9. Graph of second activation experiment of AML cond-siRNA (68 hr). Two-fold activation was seen. There is a 14-fold difference between the ON and OFF constructs.*

Fig. 18

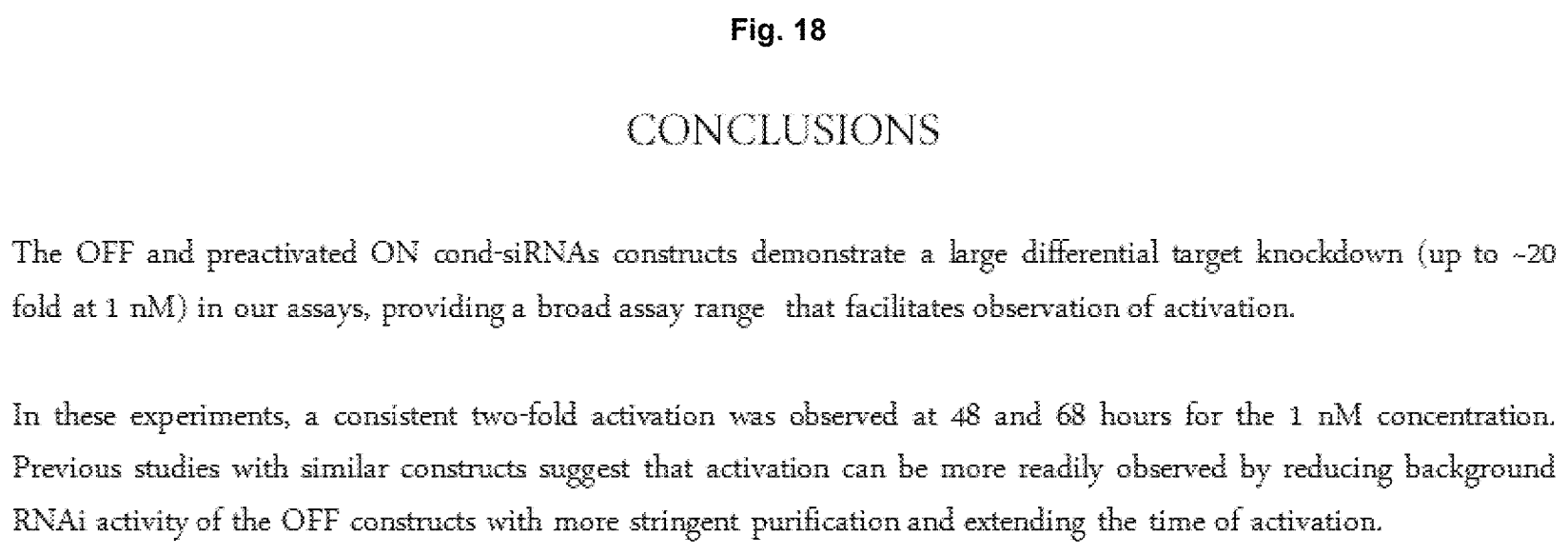

CONCLUSIONS

The OFF and preactivated ON cond-siRNAs constructs demonstrate a large differential target knockdown (up to ~20 fold at 1 nM) in our assays, providing a broad assay range that facilitates observation of activation.

In these experiments, a consistent two-fold activation was observed at 48 and 68 hours for the 1 nM concentration. Previous studies with similar constructs suggest that activation can be more readily observed by reducing background RNAi activity of the OFF constructs with more stringent purification and extending the time of activation.

Fig. 19

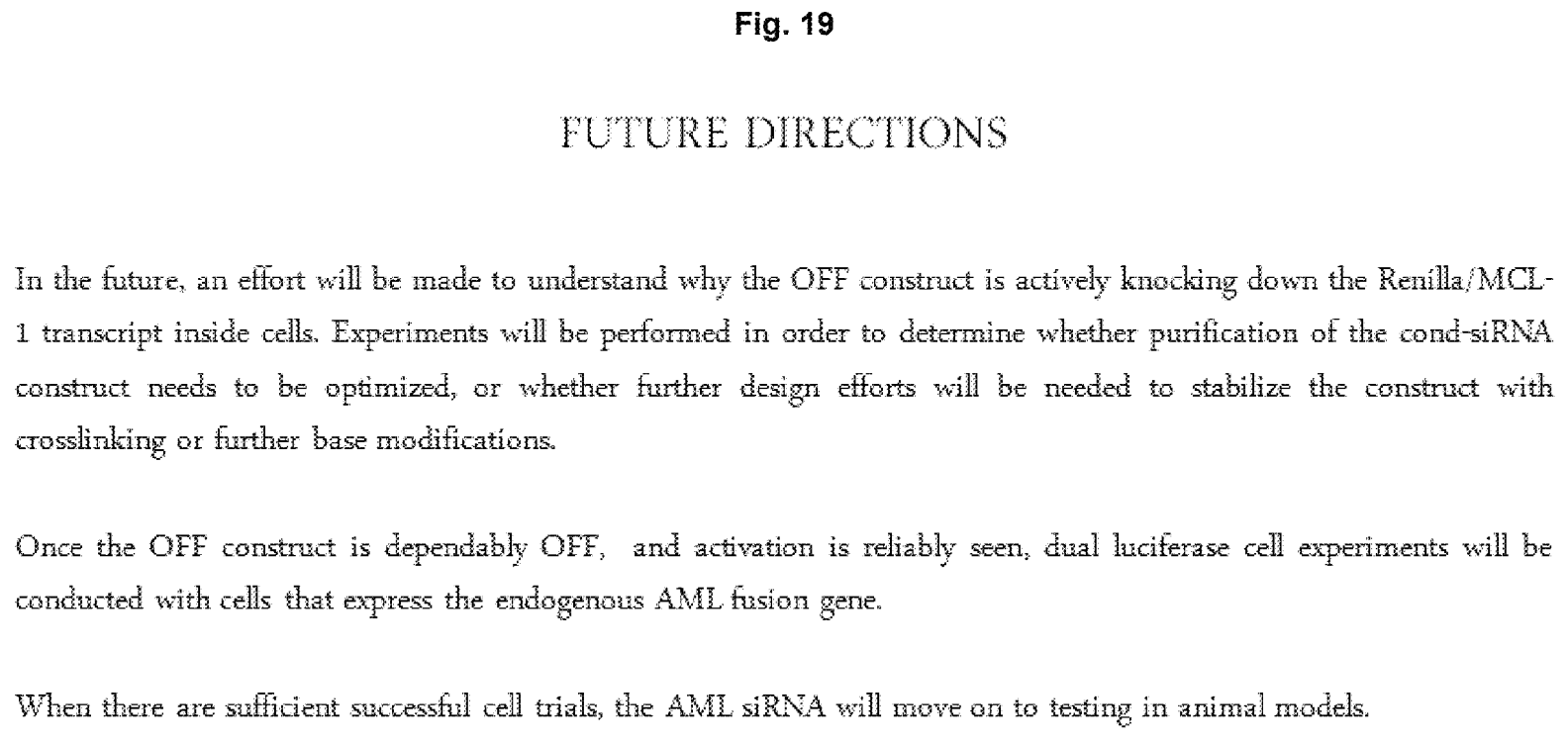

FUTURE DIRECTIONS

In the future, an effort will be made to understand why the OFF construct is actively knocking down the Renilla/MCL-1 transcript inside cells. Experiments will be performed in order to determine whether purification of the cond-siRNA construct needs to be optimized, or whether further design efforts will be needed to stabilize the construct with crosslinking or further base modifications.

Once the OFF construct is dependably OFF, and activation is reliably seen, dual luciferase cell experiments will be conducted with cells that express the endogenous AML fusion gene.

When there are sufficient successful cell trials, the AML siRNA will move on to testing in animal models.

Fig. 20

Leukemic blast death over time after loss of MCL-1

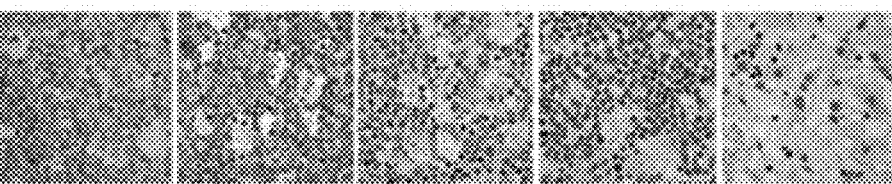

*http://genesdev.cshlp.org/content/26/2/120.full*

Cond-siRNA Activation Trial Knockdown

Graph of cond-siRNA Knockdown of target relative to controls. The most knockdown seen in 48%.

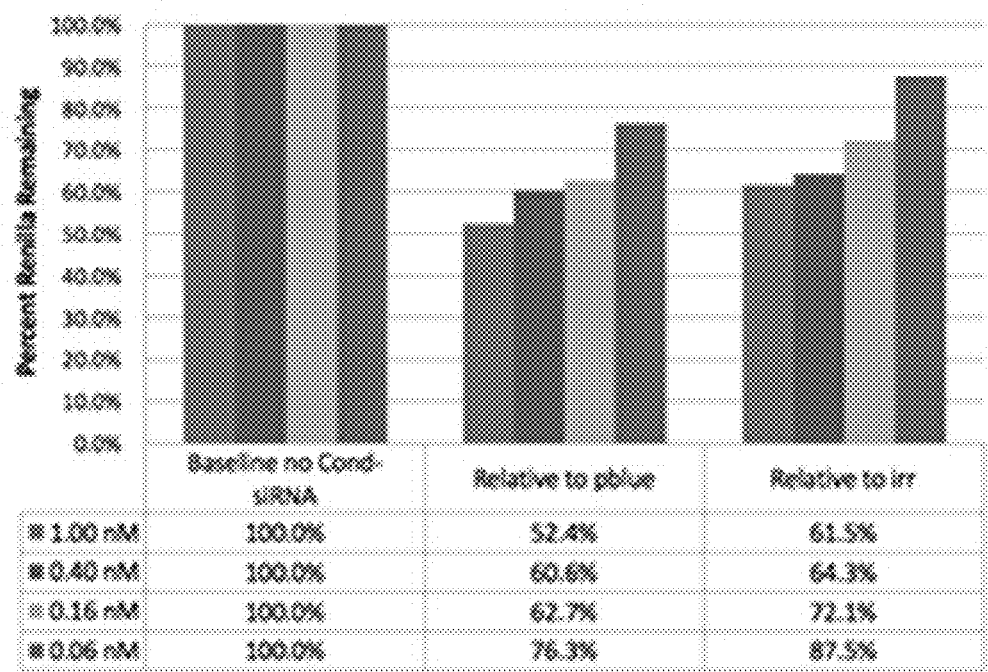

| | Baseline no Cond-siRNA | Relative to gblue | Relative to irr |
|---|---|---|---|
| 1.00 nM | 100.0% | 52.4% | 61.5% |
| 0.40 nM | 100.0% | 60.6% | 64.3% |
| 0.16 nM | 100.0% | 62.7% | 72.1% |
| 0.06 nM | 100.0% | 76.3% | 87.5% |

REFERENCES
1. "What are the key statistics about acute myeloid leukemia" *American Cancer Society*. 5 Jan. 2017, https://www.cancer.org/cancer/acute-myeloid-leukemia/about/key-statistics.html. Accessed 24 July 2017.
2. Look, Thomas A. "Oncogenic Transcription Factors in the Human Acute Leukemias" *Science*, Vol. 278, Issue 5340, pp. 1059-1064
3. Glaser, Stefan P. et al. "Anti-apoptotic Mcl-1 is essential for the development and sustained growth of acute myeloid leukemia" *Genes & Dev.* Vol. 26 pp. 120-125

ACKNOWLEDGEMENTS

Dr. Rossi, Dr. Si-Ping Han, Dr. Lisa Scherer
Marwa BenHajSalah, Robin Hu, Sahil Sagar
Stephanie Patterson, Dr. Kate Sleeth
Sarah Bannister, Tracy Kurry
Eugene and Ruth Roberts Summer Academy
Ford Research Mentor's Endowment
Occidental College Undergraduate Research Center

28

Fig. 24B                    Fig. 24C
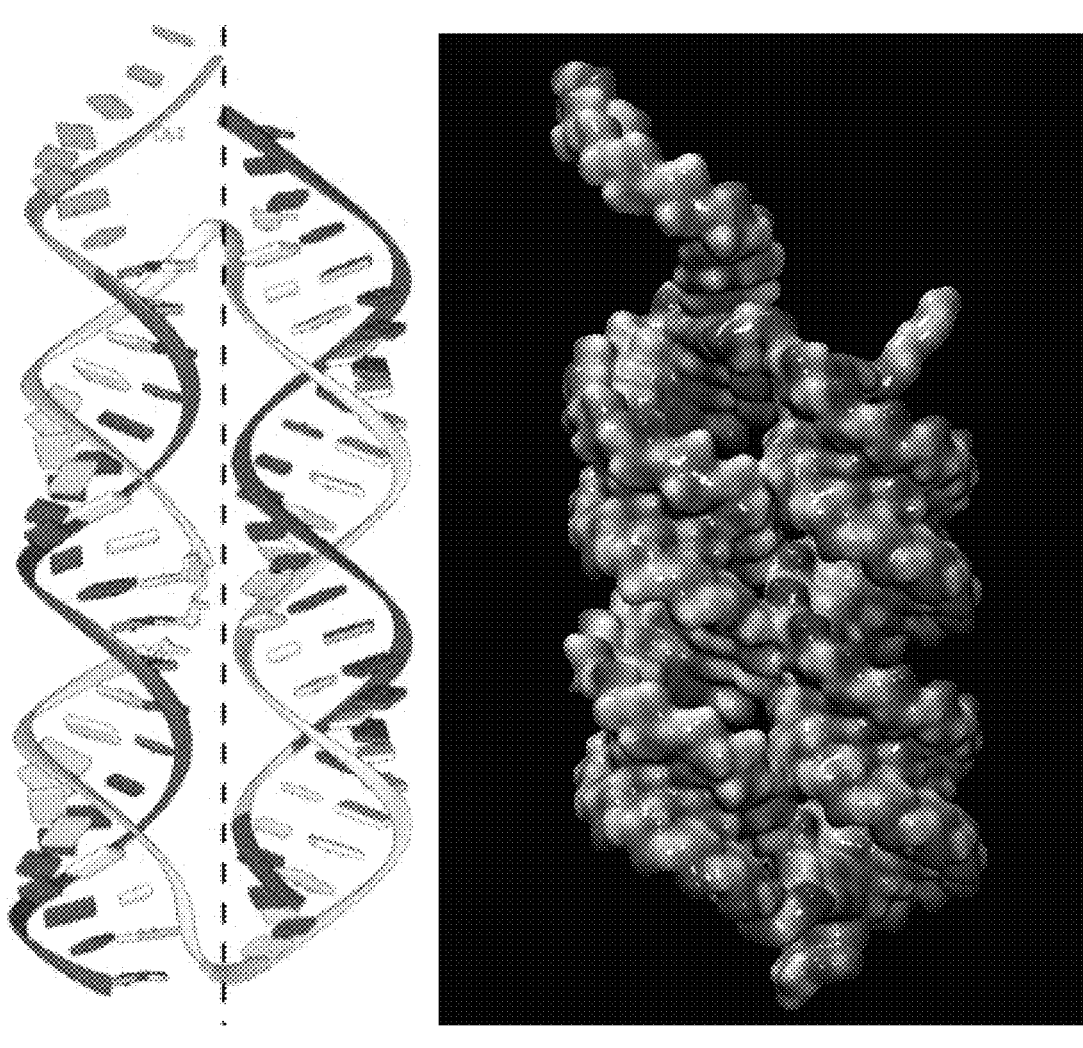

3' Sensor toehold (8 bases)

Complementary Strand A (11 or 12 bases)

Sensor strand 23 base-pair duplex

Complementary Strand B (11 or 12 base)

5' blunt end

CONDITIONAL-siRNAs AND USES THEREOF IN TREATING ACUTE MYELOID LEUKEMIA

PRIORITY CLAIM

This application is a continuation of U.S. patent application Ser. No. 16/786,793, filed Feb. 10, 2020, which is a continuation of International Application No. PCT/US2018/046383, filed Aug. 10, 2018, which claims priority to U.S. Provisional Patent Application No. 62/543,812, filed Aug. 10, 2017, the subject matter of which is hereby incorporated by reference in their entirety, as if fully set forth herein.

STATEMENT REGARDING FEDERALLY SPONSORED RESEARCH

This invention was made with government support under Grant Number 1332411, awarded by National Science Foundation through the Emerging Frontiers in Research and Innovation, Origami Design for Integration of Self-assembling Systems for Engineering Innovation (EFRI-ODIS-SEI), and Grant Number A1029329, awarded by National Institutes of Health (NIH). The government has certain rights to the invention.

SEQUENCE LISTING

This application contains a ST.26 compliant Sequence Listing, which was submitted in XML format via Patent Center, and is hereby incorporated by reference in its entirety. The XML copy, created on Mar. 27, 2023, is named 0544358175US02.xml and is 46,000 bytes in size.

BACKGROUND

RNA interference (RNAi) is a sequence-specific mRNA degradation pathway mediated by siRNA duplexes, key for cellular immunity and developmental regulation (FIG. 2). Researchers have utilized synthetic RNAi triggers for therapeutics by inhibiting a specific gene product found to be essential in disease driving pathways but non-essential for normal functioning.

Consider however that some genes essential in disease progression may have vital functions in normal cells and are dangerous to target. Meanwhile other upregulated genes are not essential for disease progression, but serve as effective indicators. Therefore, there is a need in the art to develop effective therapies to exploit this differential expression in various indications, such as Acute Myeloid Leukemia (AML).

According to the American Cancer Society, 21,380 new cases of Acute Myeloid Leukemia (AML) were diagnosed in 2017.[1] AML is a fast-moving cancer of the blood, resulting in a build-up of undeveloped white blood cells, known as blasts, and responsible for 10,590 deaths in the past year.

Current molecularly targeted cancer drugs work by inhibiting specific genes that are essential for the survival of cancer cells but non-essential to normal cells. This strategy does not work on all cancers: three recent studies in precision medicine found targetable mutations in 10%[2], 45%[2], or 75% of late stage patients [3]. Even when cancer specific drug targets are present, the heterogeneity of cancer cells in late stage disease often leads to rapid development of drug resistance [4]. Thus, in clinical practice, current approaches have significant limitations and therefore, a more effective treatment is needed. The compositions, constructs, and techniques disclosed herein satisfy this need.

BRIEF DESCRIPTION OF THE DRAWINGS

FIG. 2A shows an example of a basic design of Cond-siRNAs. FIG. 2B illustrates how sensor duplexes block Dicer binding.

FIGS. 6-20 show various panels of Appendix A.

FIGS. 24A-C: A) General construct design of cond-siRNA with sensor strand designed reverse comp. to signal gene mRNA, core strand with nick either 11 or 12 bp from toehold end on sensor side designed comp. to sensor and guide, and guide strand designed reverse comp. to target gene mRNA. B) Model of cond-siRNA. C) Molecular simulation of cond-siRNA.

DETAILED DESCRIPTION

Overview of Conditional-siRNA

Described herein are conditional siRNA complexes (also referred to herein as Cond-siRNA, a conditional RNA-sensor, or an RNA-sensor) that include a therapeutic component (e.g., siRNA molecule) associated with a molecular sensor via a core molecule. The conditional siRNA complexes are inactive under normal conditions, but are activated upon interaction between the molecular sensor and a biomarker. Such molecules are synthetic riboswitch molecules that allow an input gene or RNA molecule to "switch on" an RNAi pathway against a target output gene.

Figure 21:
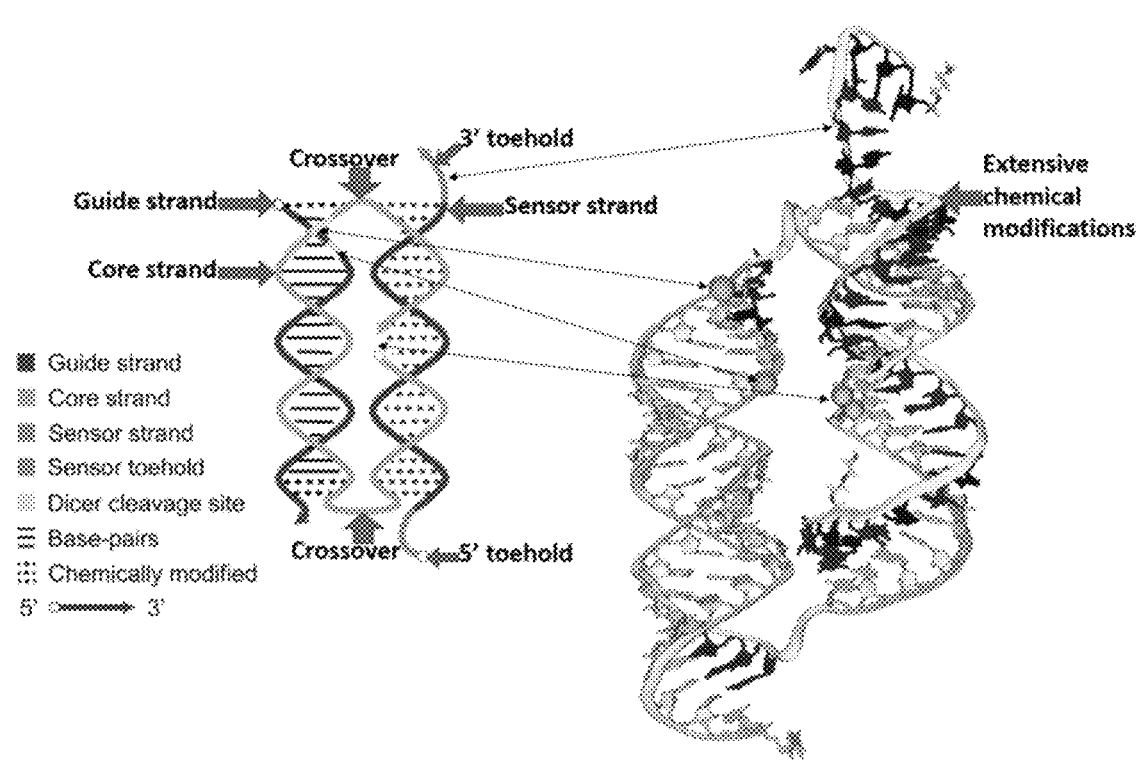
FIG. 21 shows a comparison of secondary and tertiary structure (from full atomistic MD simulations) of a Cond-siRNA construct according to one embodiment. Black arrows show corresponding features between the 2D and 3D representations.
Figure 22:
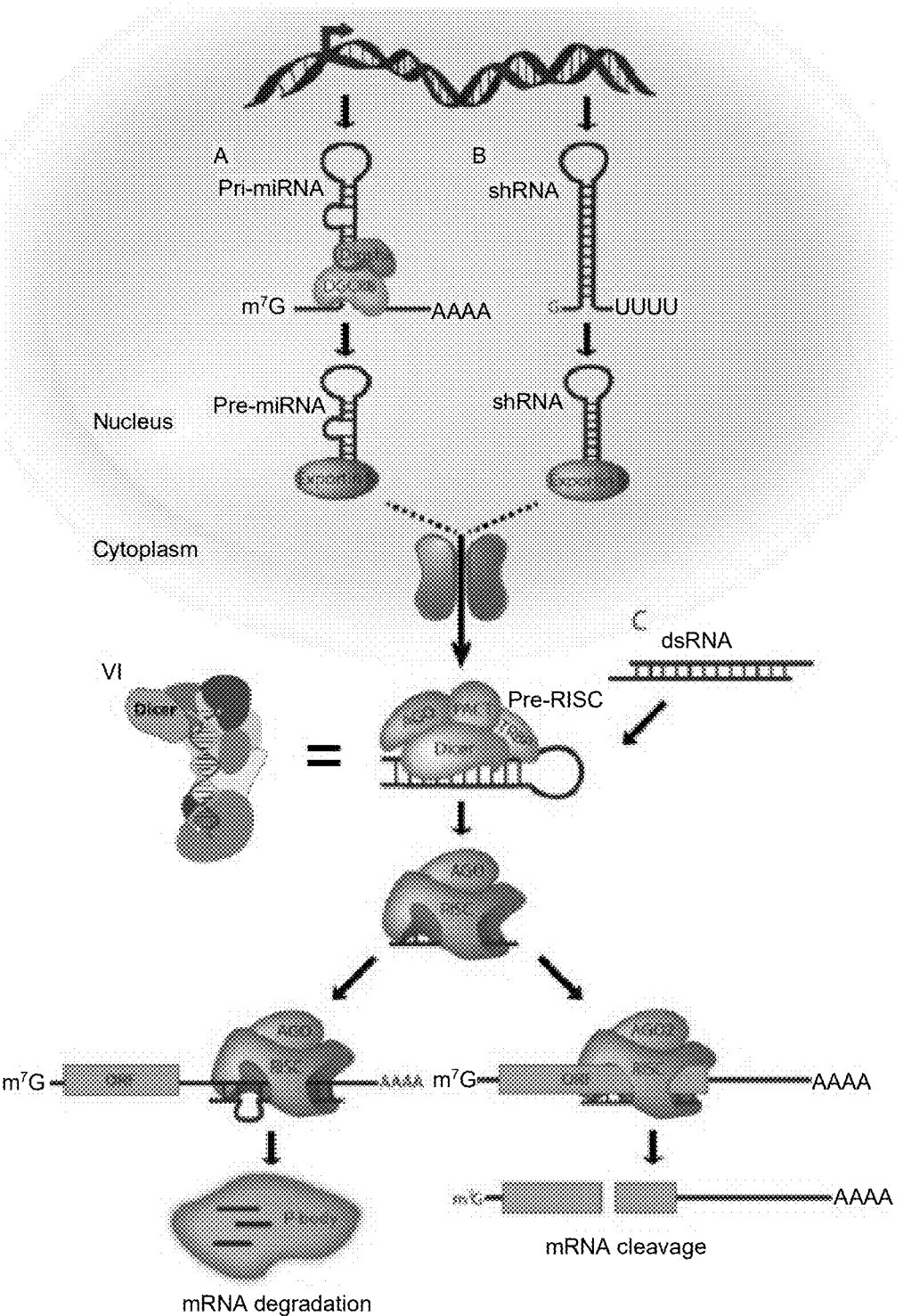
FIG. 22 is a diagram showing the RNAi pathway.

An RNA-sensor molecule or complex includes sensor strand, a guide strand, and a core strand that bind to each other to form a multi-strand molecular complex having a dual duplex structure shown in FIG. 21. In certain embodiments, those three strands (core, sensor and guide) form two parallel oligonucleotide duplexes connected in a double crossover configuration. [14] (See FIG. 21). In some aspects, the length of each of the oligonucleotide duplexes is sufficient to operate within the RNA interference (RNAi) pathway (See FIG. 22). For example, the duplexes may be between about 15 and 30 base pairs in length. In some embodiments, the duplexes are between 15 and 20 base pairs in length, between 20 and 25 base pairs in length, between 25 and 30 base pairs in length. In other embodiments, the duplexes are about 15, 16, 17, 18, 19, 20, 21, 22, 23, 24, 25, 25, 26, 27, 28, 29, 30, or more than 30 base pairs in length.

The double crossover configuration as shown in FIG. 21 represents the inactive or "OFF" state of the RNA-sensor complex wherein the sensor duplex inhibits RNAi loading of the siRNA duplex, serving as a "lock" on RNAi activity. In the OFF state, the guide strand binds a first portion (or "passenger" segment) of the core strand to form an siRNA duplex that serves as a pro-RNA molecule. The pro-RNA molecule operates in the RNAi pathway of a target cell to alter expression of a target gene or target RNA molecule associated with a pathological condition (i.e., the "therapeutic target molecule"). The second duplex is formed by the sensor strand binding to a second portion (or "protection" segment) of the core strand to form the sensor duplex. In some embodiments, the core strand has a third portion (or "protection" segment) that binds the sensor strand. In certain such embodiments, the core strand includes the passenger strand (P) that is joined to first and second protection segments (A, B) at each end by a linker (L1, L2) in the following configuration:

5'B-L2-P-L1-A3'.

The sequence of the core strand is determined by the sequences of the sensor and guide strands, and may be fully or complementary to the sensor strand, the guide strand, or both. Any suitable linker can be used in accordance with the embodiments described herein, including, but not limited to, an internal C3 spacer, a C6 linker, a tri-ethylene glycol linker.

The RNA-sensor complex is activated to the "ON" state upon interaction with a biomarker in the cell expressing a phenotype associated with the pathological condition targeted by the guide strand of the siRNA duplex. This activation is primarily due to the design of the sensor strand, which serves as the activation signal for RNAi activity. When this is the case, the RNA-sensor complex is said to detect the biomarker.

Figure 23:
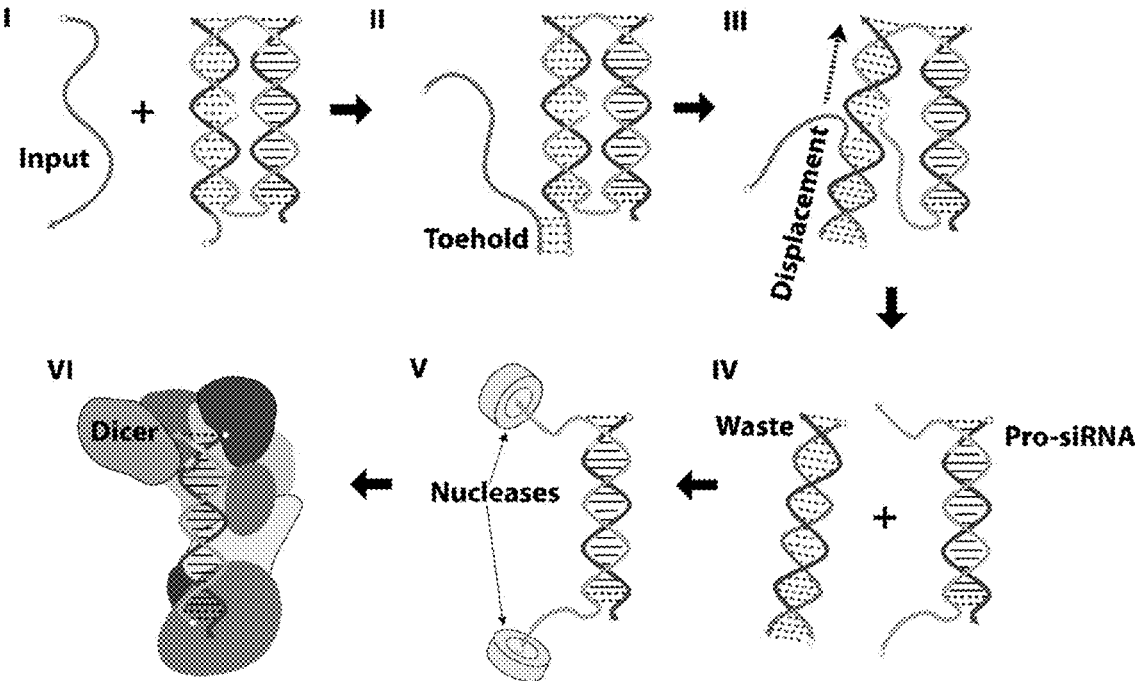
FIG. 23 shows toehold mediated strand displacement process of conditional siRNA. In step I, c-siRNA meets RNA transcript with correct activation sequence (Input). In step II, an Input RNA binds to the toehold. Step III shows toehold mediated strand displacement. Step IV shows the sensor strand and input forming a waste duplex that separates from the pro-siRNA. In step V, XRN1, exosome and other cytosolic RNAses rapidly degrade unprotected overhangs, turning pro-siRNA into efficient Dicer substrate. In step VI, siRNA is processed by Dicer for incorporation into RISC. The basic biophysical process of toehold mediated strand displacement includes a fast 1D random walk: uS to mS for each of N^2 steps. This results in sequence specificity from both toehold and duplexes. Thermodynamically stable chemical modifications are confined to sensor strand to avoid kinetic traps.

The sensor strand includes a nucleotide sequence designed to bind the biomarker associated with the pathological condition (i.e., "pathological biomarker"). Binding to the biomarker is initiated by the binding of at least one toehold segment (single stranded) to an input RNA strand that encodes at least a portion of the pathological biomarker, as shown in FIG. 23. Upon displacement of the sensor strand, the sensor and input strands from a waste duplex that separates from the pro-siRNA molecule, allowing the pro-siRNA to be processed by the target cell's RNAi system. The structure and binding dynamics of the conditional-siRNAs described herein is explained further in U.S. Pat. No. 9,725, 715, the content of which is incorporated herein by reference in its entirety.

The sequence of the sensor strand can be fully or partially complementary to an RNA sequence present in the pathological biomarker. In certain embodiments, the sensor strand is 100% complementary to the RNA sequence present in the pathological biomarker. Other embodiments may include a sensor strand that is largely complementary to the RNA sequence present in the pathological biomarker, for example, the sensor strand may be greater than 70% complementary, greater than 75% complementary, greater than 80% complementary, greater than 85% complementary, greater than 90% complementary, greater than 95% complementary, greater than 96% complementary, greater than 97% complementary, greater than 98% complementary, or greater than 99% complementary to the RNA sequence present in the pathological biomarker.

In some embodiments, the pathological biomarker is an RNA sequence that forms or encodes a molecule that is associated with the pathologic condition. In some aspects, the pathological biomarker is an RNA sequence that is present in the target cell under pathological conditions, but is substantially absent under normal conditions. Alternatively, the pathological biomarker is an RNA sequence that is upregulated in the target cell under pathological conditions as compared to normal conditions.

The guide strand includes a Dicer cleavage site near the 3' end. The sequence between the Dicer cleavage site and the 3' terminus of the guide strand is either fully or partially complementary to a nucleotide sequence found in the therapeutic target molecule (e.g., target gene, target mRNA or target miRNA). When this is the case, the Cond-siRNA is said to target the gene or RNA molecule. In certain embodiments, the guide strand is 100% complementary to the nucleotide sequence found in the therapeutic target molecule. Other embodiments may include a guide strand that is largely complementary to the nucleotide sequence found in the therapeutic target molecule, for example, the guide strand may be greater than 70% complementary, greater than 75% complementary, greater than 80% complementary, greater than 85% complementary, greater than 90% complementary, greater than 95% complementary, greater than 96% complementary, greater than 97% complementary, greater than 98% complementary, or greater than 99% complementary to the nucleotide sequence found in the therapeutic target molecule.

A challenge of using oligonucleotides in vivo lies in preventing nuclease degradation of RNA nucleotides. Several chemical modifications in the sensor strand can be used to overcome this challenge. For example, Locked Nucleic Acids (LNAs) include a modification of RNA nucleotides with an extra bridge between the 2' O and 4' C increases thermal stability of RNA duplexes and allows for resistance to nucleases. 2' O-Methyl modifications confer stability, increase binding affinity to RNA nucleotides and prevent degradation by nucleases. And, phosphorothioate: modification by replacing one of the non-bridging oxygens in the phosphate linkage between bases with a sulfur that reduces nucleolytic degradation; however also lowers binding affinity.

Thus, in certain embodiments, the RNA-sensor complex includes one or more modifications to the nucleotide sequence of the sensor strand, the core strand, and/or the guide strand. Exemplary modifications that may be used include, but are not limited to, locked nucleic acids (LNA), peptide nucleic acids (PNA), 2'-O-methyl modifications, morpholino modifications, phosphorothioate modifications, terminal modifications, and other linker or backbone modifications or connections. Additional chemical modifications may be chosen according to methods described in US972571562, the disclosure of which is hereby fully incorporated herein.

Figure 24A:
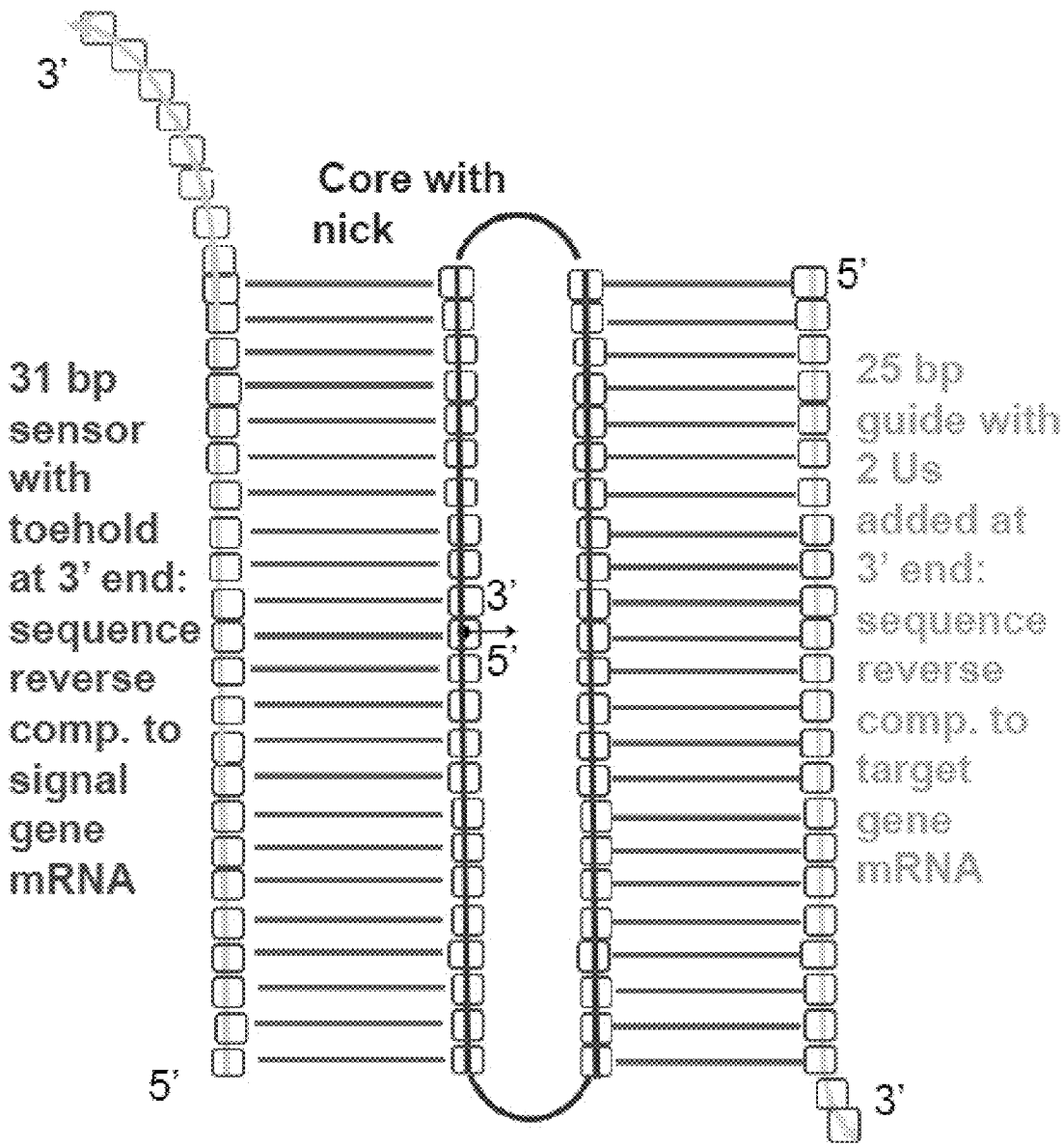

The approach of designing a cond-siRNA sensor complex for use in treating a disease or other pathological condition using the cond-siRNA sensor complexes is advantageous in that it allows the complex to become biologically active only in diseased cells AND remain OFF in healthy cells. In addition, the approach allows for increased disease cell specificity and prevents toxicity from delivery to unintended off-targets. Further, the approach combines disease specificity from one gene with treatment efficacy from a second gene to create therapeutics that are precisely tailored to specific gene expression patterns. Still further, the approach is advantageous due to steric hindrance of the two RNA duplexes positioned in a parallel configuration (FIG. 24). The sensor strand inhibits RNAi loading of siRNA and will only displace when activated in disease cells.

Overview of Methods for Designing a Conditional siRNA Complex

An siRNA complex is designed based on biomarkers and therapeutic target molecules that are specific to each cell type, pathological condition, and/or indication. According to certain embodiments, methods for designing and testing each conditional siRNA complex includes several steps, as described below.

Figure 25:
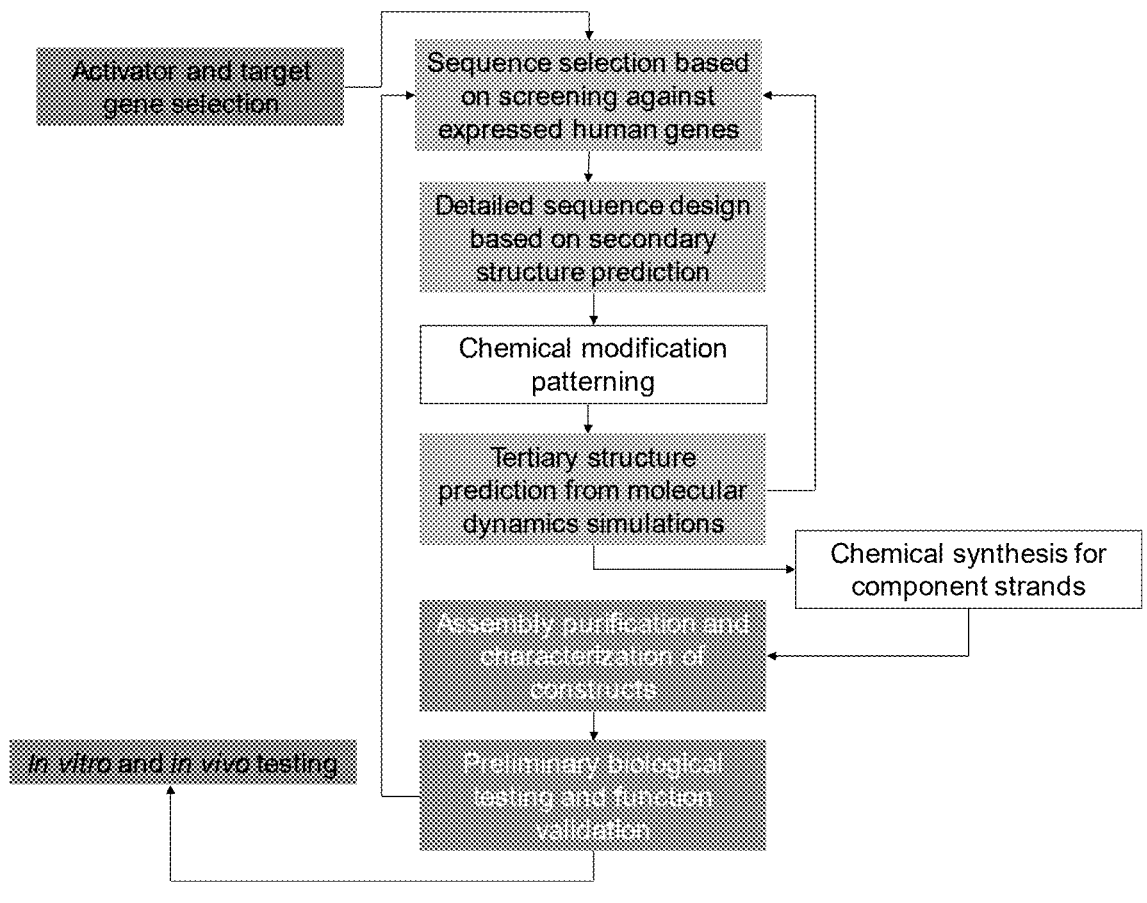
FIG. 25 shows an overview of the design process for Cond-siRNAs according to one embodiment.
Figure 26:
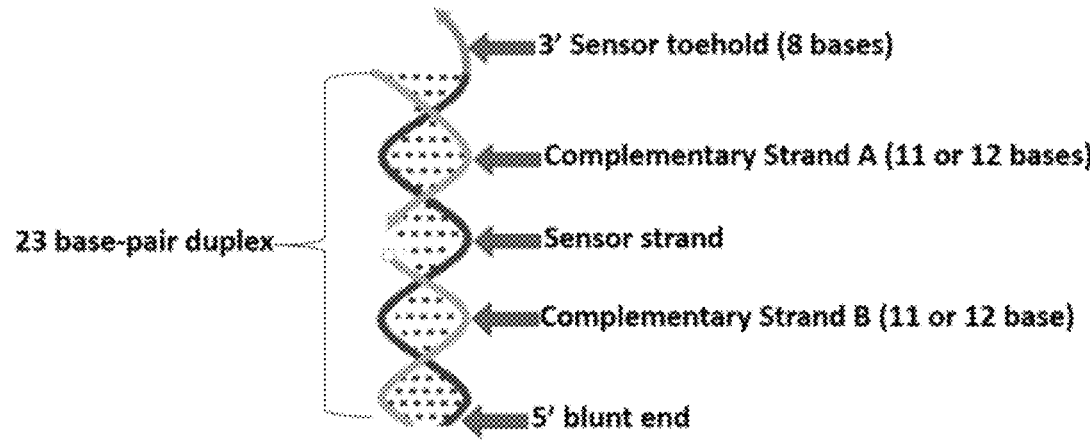
FIG. 26 shows a hypothetical sensor duplex for mRNA used to check for thermodynamic stability of the sensor according to one embodiment.
Figure 27:
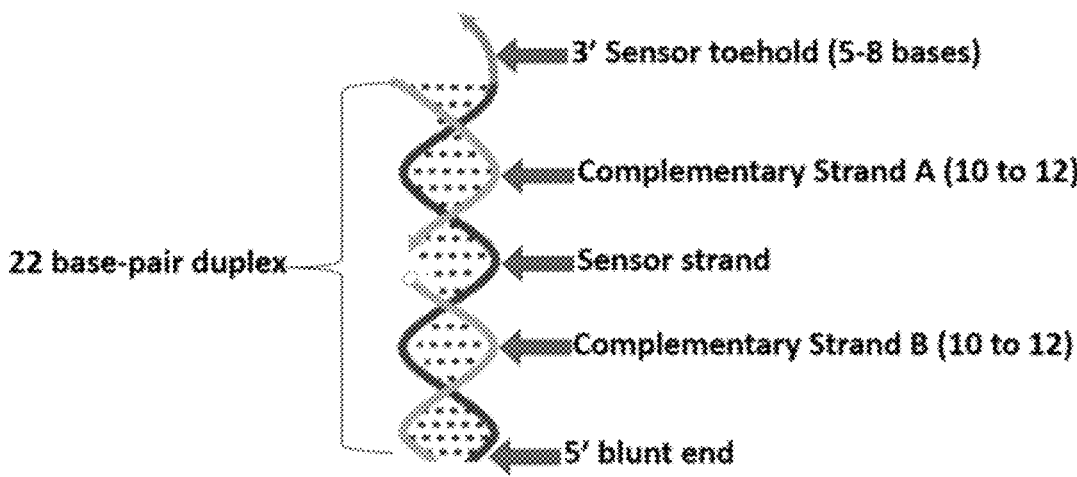
FIG. 27 illustrates a cond-siRNA construct disclosed herein.

FIG. 25 shows an overview of the design process. In certain embodiments methods for designing a conditional siRNA complex (the "design method") includes a step of determining a biomarker that will serve as an input for activation and a therapeutic target for RNAi inhibition. This step may include a determining one or more factors that are differentially expressed (i.e., upregulated or present in a diseased cell as compared to a normal cell) using methods known in the art.

The design method further includes a step of generating a list of candidate target segments of the biomarker (i.e., target mRNA sequence or target miRNA sequence) that can serve as a biomarker segment for binding the sensor strand, and then designing sensor strands for each biomarker.

The design method further includes a step of estimating the thermodynamic stability of the resulting sensor strand-biomarker duplexes (the sensor duplex) generated by the target segments and sensor strands by using secondary structure prediction tools used in the art [15].

The design method further includes a step of checking for the uniqueness of the binding site for the most stable sensor duplexes against the known transcriptome of the animal to which the conditional siRNA complex will be tested against.

The design method further includes a step of generating a list of guide strand sequences by using a protocol that may include, but is not limited to, standard siRNA design tools, literature references, or heuristic rules.

The design method further includes a step of creating a Dicer substrate from the chosen guide strand sequences.

The design method further includes a step of generating sequences for the core strand that connect the sensor strands to the guide strands.

The design method further includes a step of checking that the sensor: guide pairing does not create unwanted interactions.

The design method further includes a step of selecting a pattern of suitable chemical modifications as described herein, and optionally simulating the constructs using molecular simulation methods used in the art to simulate the constructs (optional).

The design method may also include a method of synthesizing or purchasing the sensor, core, and guide strands from commercial vendors such as Qiagen, Dharmacon, or IDT, the constructs of which are then assembled, characterized, and purified using gel electrophoresis.

The design method further includes a step of conducting preliminary biological testing and validation of the construct function, and then optionally test in in vitro and in vivo models of pathological conditions, including, but not limited to, MI induced maladaptive hypertrophy as described below.

Additional embodiments related to designing the guide, the sensor and the core strands are explained below.

Method for Designing Sensor Strands for mRNA Biomarker

According to certain embodiments, methods for designing and testing sensor strands that target an mRNA biomarker includes an algorithm that includes several steps, as described below.

In certain embodiments, a method for designing a sensor strand for an mRNA biomarker (the "mRNA sensor design method") includes a step of identifying the 3' UTR for each messenger RNA biomarker.

The mRNA sensor design method further includes a step of generating all possible consecutive 31 base sequences for each 3' UTR identified above.

The mRNA sensor design method further includes a step of obtaining the prospective sensor strand sequence for each sequence segment from the previous step by identifying the reverse complement (full or partial) of each sequence.

The mRNA sensor design method further includes a step of checking each sensor strand sequence for the following undesirable features: (i) three or more consecutive Gs, and (ii) four or more consecutive A or U bases.

The mRNA sensor design method further includes a step of checking each sensor strand sequence for the following desirable features: (i) higher than 50% G/C bases—this correlates with thermodynamic stability, (ii) "three lettered-ness," (iii) The first base at the 5' end of the sensor strand is a C or a G; and (iv) the 9th base from the 3' end of the sensor strand is a C or a G. According to the embodiments described herein, "three letteredness" is defined as the proportion of the sequence comprising of the three most numerous bases (e.g., the extent to which sequence is mostly made of A, U, C; or C, G, A; or A, U, G). A higher three letteredness score correlates with lower internal secondary structure.

The mRNA sensor design method further includes a step of ranking all possible sensor strands. Strands with the least number of features from 4 and the highest scores from 5 are ranked highest.

The mRNA sensor design method further includes a step of generating hypothetical sensor duplexes using the pattern, starting from the highest ranked strands.

The RNA sensor design method further includes a step of using Nupack or similar secondary structure prediction codes to calculate the following, starting from the highest ranked strands: (i) the internal secondary structure of the sensor strand (lower amounts of internal secondary structure are desirable, (ii) the thermodynamic stability of the hypothetical duplex from 7. Ideally, at 1 nM strand concentration, Nupack should predict that >90% or >95% of component strands should form the hypothetical sensor duplex; and (iii) if sensor duplex is not stable, can adjust 1 to 5 bases at the 5' terminus of the sensor sequence to increase stability at the cost of reducing complementarity to the corresponding binding site on the putative biomarker.

The RNA sensor design method further includes a step of screening the sensor strand for thermodynamically stable duplexes using NCBI BLAST according to the following parameters: (i) use the "somewhat similar" search option, (ii) for sensor sequences, the 8 bases at the 3' terminus (constituting the 3' toehold) should have no more than 5 bases complementary to known transcripts in the target animal (eg, human or mouse) other than the intended bio-marker, and (iii) if the first two criteria not met, broaden sequences considered in 1 to the coding region or the entirety of the mRNA.

Method for Designing Sensors for miRNA Biomarker

According to certain embodiments, methods for designing and testing sensor strands that target an miRNA biomarker includes an algorithm that includes several steps, as described below.

In certain embodiments, a method for designing a sensor strand for an miRNA biomarker (the "miRNA sensor design method") includes a step of identifying a guide sequence for each miRNA biomarker, to which the sensor strand is designed to bind (typically approximately 21 bases according to one aspect).

The miRNA sensor design method further includes a step of obtaining the reverse complement (full or partial) of the miRNA guide sequence.

The miRNA sensor design method further includes a step of adding 8 more bases to the 5' end of the sequence from the prior step.

The miRNA sensor design method further includes a step of generating hypothetical sensor duplexes, starting from the sequence developed in the prior step.

The miRNA sensor design method further includes a step of using Nupack or similar secondary structure prediction codes to calculate the following: (i) the thermodynamic stability of the hypothetical duplex from the prior step. Ideally, at 1 nM strand concentration, Nupack should predict that >90% or >95% of component strands should form the hypothetical sensor duplex. (ii) if sensor duplex is not stable or the secondary structure is incorrect, determine whether the 8 terminal bases at the 5' end of the sensor strand, or the length of strand A or strand B can be altered or modified to optimize thermodynamic stability.

The miRNA sensor design method further includes a step of screening the sensor strand for thermodynamically stable duplexes in NCBI BLAST according to the following parameters: (i) use the "somewhat similar" search option, (ii) for sensor sequences, the 8 bases added at the 5' end of the sensor should not increase complementarity to tran-scripts other than the intended miRNA. If they do, adjust the sequence and start over from 4.

Methods for Designing a Guide Strand Sequence Against a Therapeutic Target Molecule According to certain embodiments, methods for designing a guide strand sequence against a therapeutic target gene or RNA molecule (e.g., mRNA or miRNA) includes several steps, as described below.

In certain embodiments, a method for designing a guide strand sequence against a therapeutic target (the "guide strand design method") includes a step of obtaining one or more prospective guide strand sequences using at least one of the following methods: (i) find a published guide strand sequence for the intended target; (ii) find a known miRNA target site on the target gene, or (iii) use a published algorithm or design tool known in the art [17,18].

The guide strand design method further includes a step of checking the guide sequence to make sure that the 6 bases at the 5' domain is more AU rich than the 6 bases in the 3' domain. This will improve probability for correct strand loading [19]. Ideally, the 3' domain should be CG rich, and terminate in a CG base-pair.

The guide strand design method further includes a step of adding four terminal bases to the 5' end of the guide strand to complete the duplex. Those should be CG rich to improve thermodynamic stability.

The guide strand design method further includes a step of constructing the hypothetical RNAi targeting duplex.

The guide strand design method further includes a step of checking that the guide strand has weak internal secondary structure and minimal tendency to bind to itself (no more than 10% at 1 nM strand concentration) using Nupack or similar standard secondary structure calculation tool. Adjust bases added in 3 as necessary.

Methods for Designing a Core Strand Sequence and Check-ing Compatibility of Pairing Sensor to Guide According to certain embodiments, methods for designing a core strand sequence and checking compatibility of pairing sensor to guide includes several steps, as described below.

In certain embodiments, a method for designing a guide strand sequence against a therapeutic target (the "core strand design method") includes a step of choosing a suitable combination of sensor and guide strands, methods for designing those strands are discussed above and in the working examples, according to the embodiments described herein.

Figure 10:
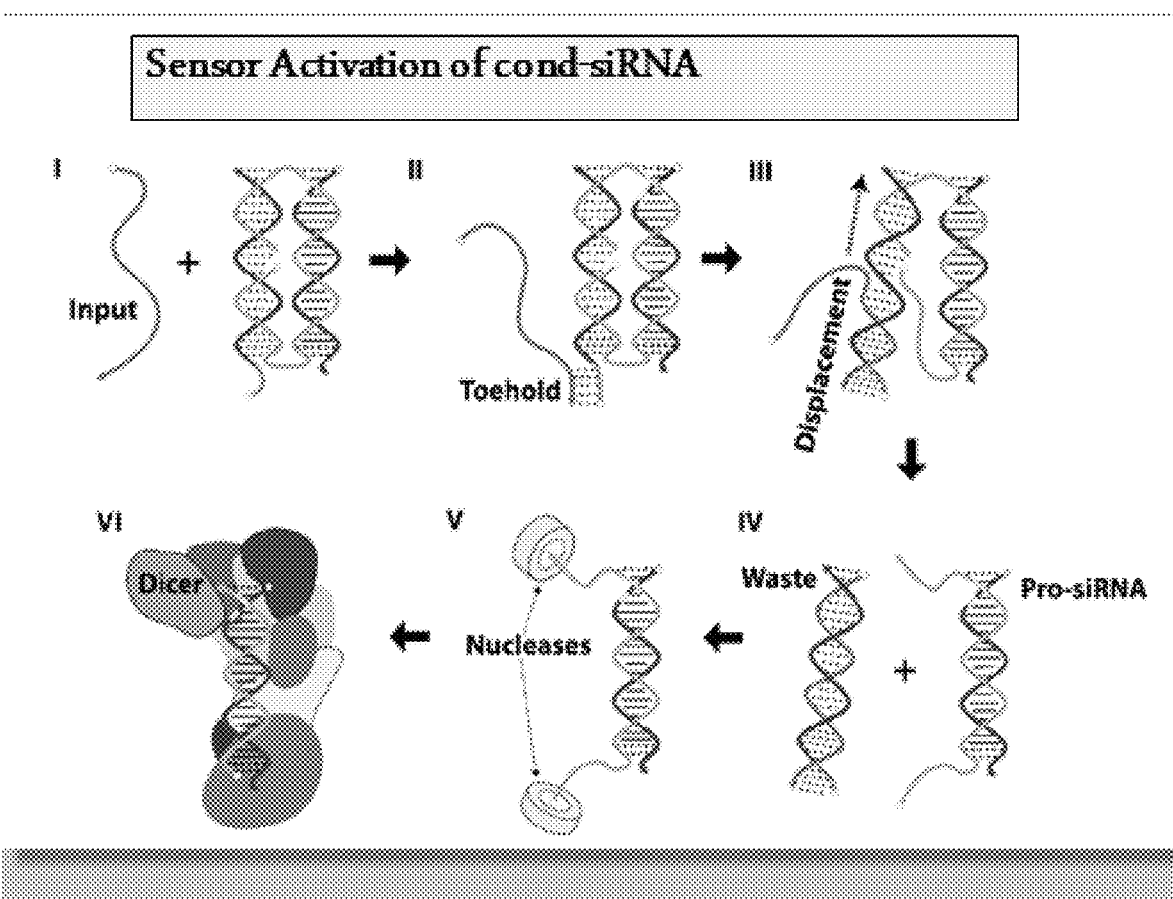
Figure 11:
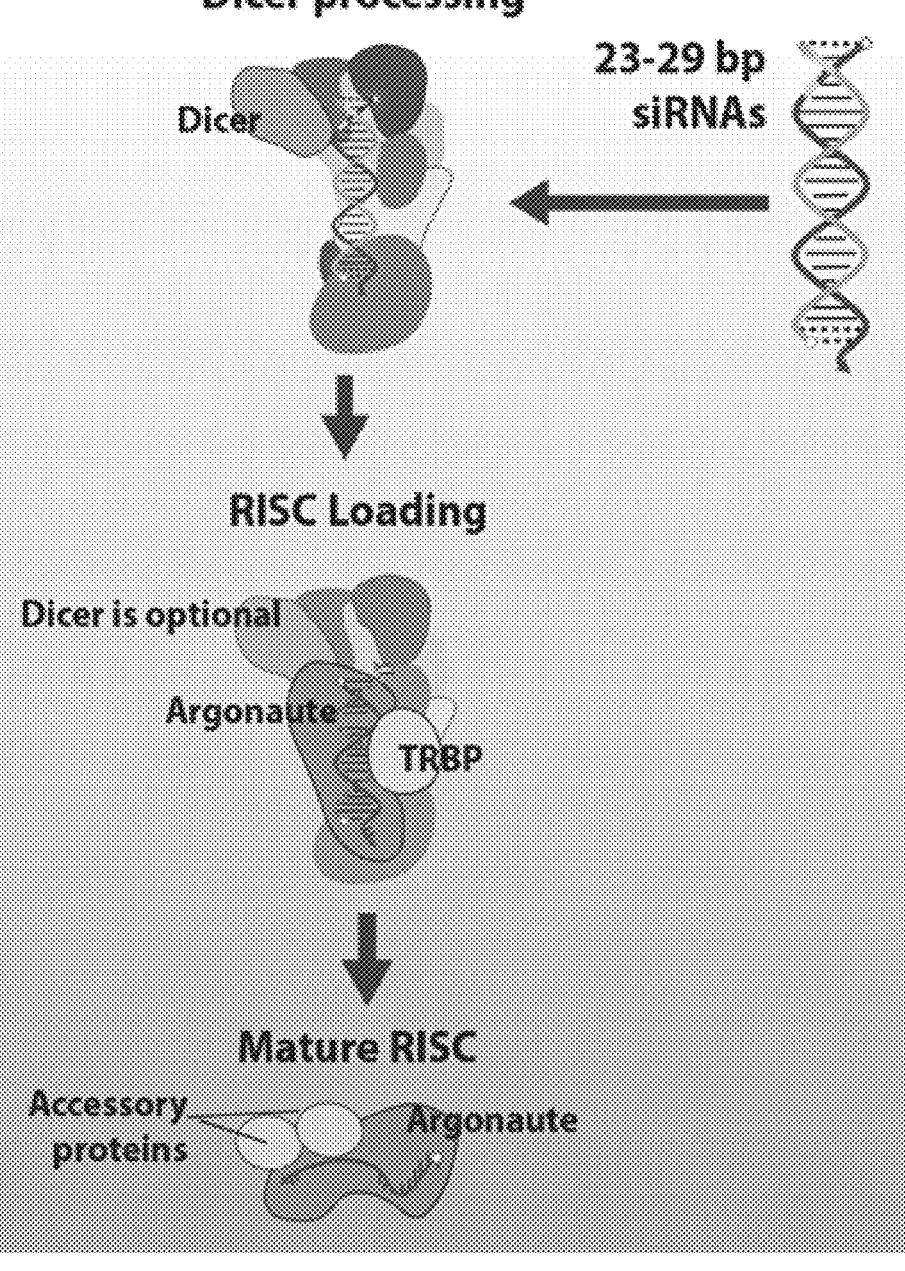
Figure 12:
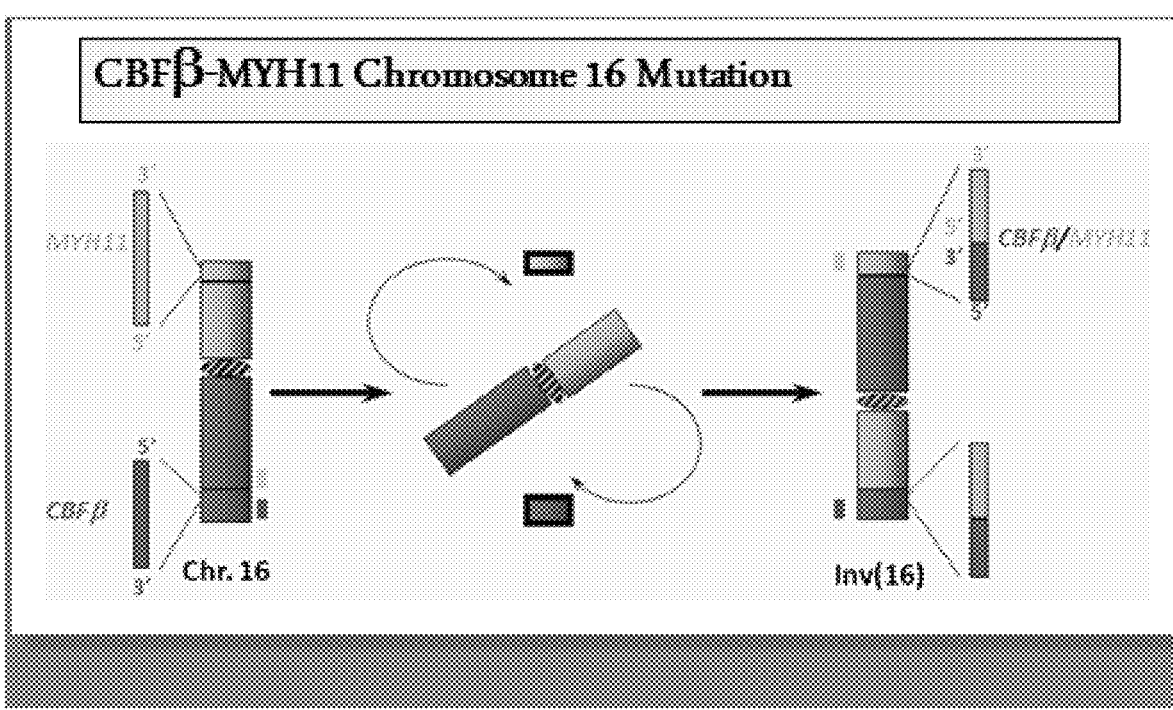
Figure 15:
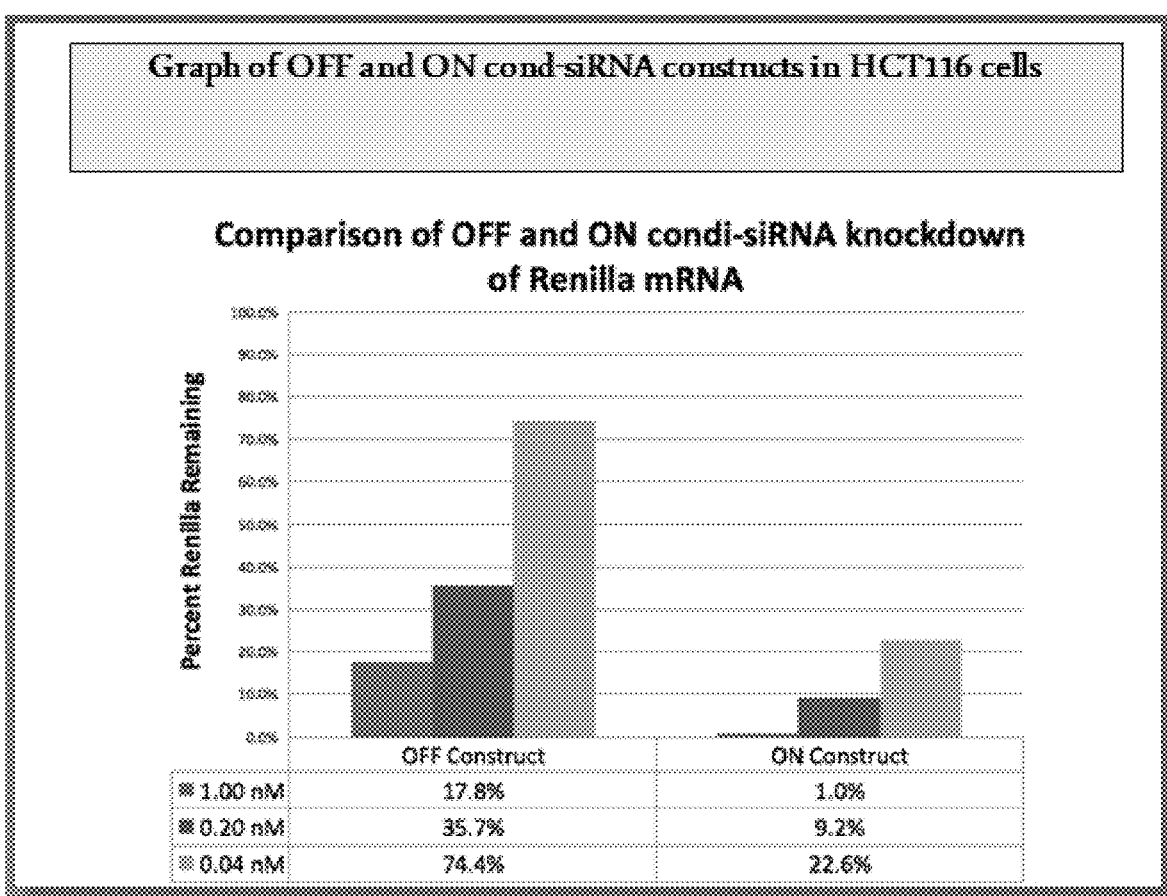
Figure 16:
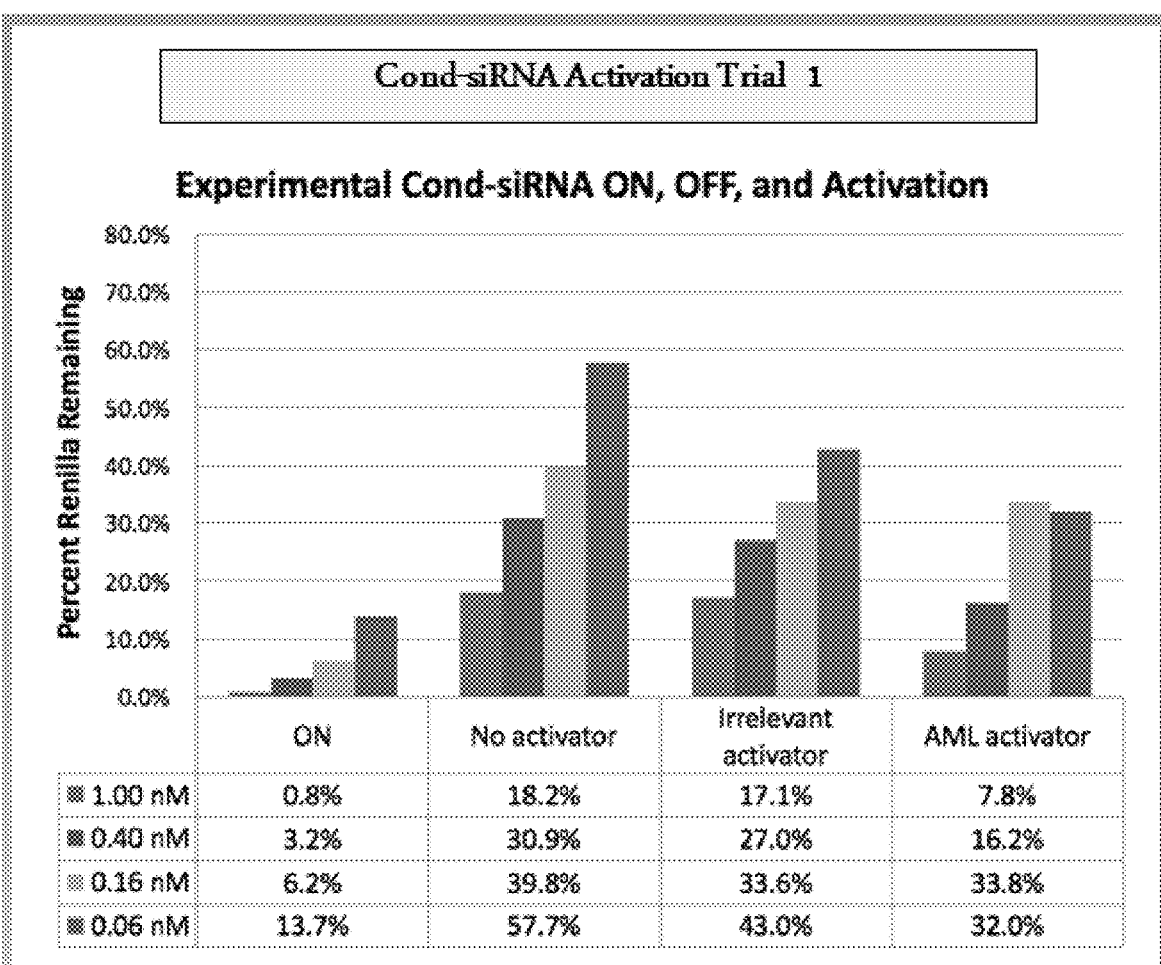
Figure 17:
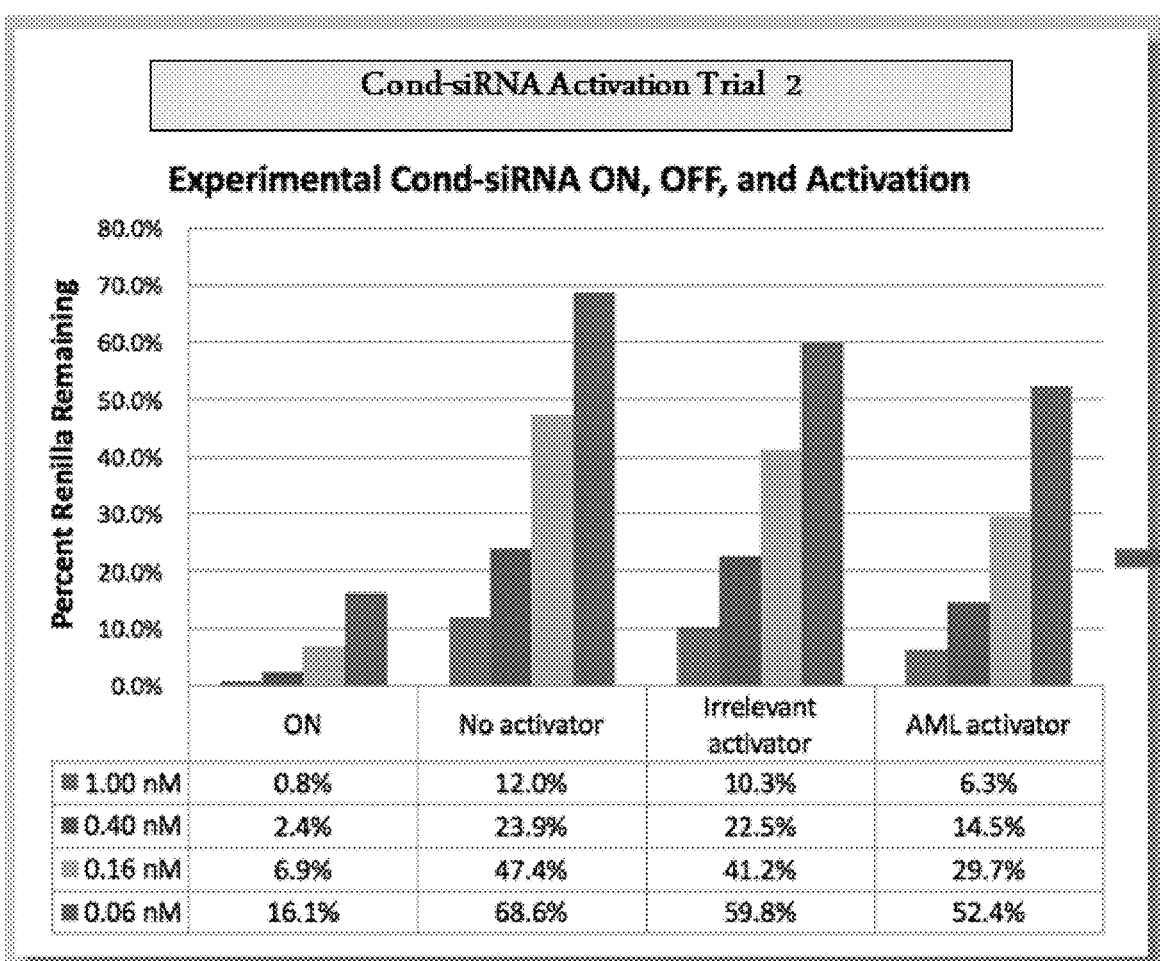

The core strand design method further includes a step of constructing the core strand by constructing a strand of the form 5'-B-C3-P-C3 A-3' where A and B are the sequence of complementary strand B from the hypothetical sensor duplex (FIG. 6 or 9), P is the sequence of the passenger strand from the hypothetical RNAi duplex (FIG. 10) and C3 are C3 linkers.

The core strand design method further includes a step of using Nupack or similar standard secondary structure cal-culation tool to check that the guide strand and core strand base-pairing has the following properties: (i)>95% of strands are base-paired in the correct duplex at 1 nM strand concentration, (ii) the guide strand duplex has the correct conformation, with a ~23 base-pair duplex, a two base 3' guide strand overhang, and 10-12 base 5' and 3' core overhangs with minimal secondary structures, and (iii) If above criteria not met, choose new sensor or guide pairing.

Conditional siRNA Complexes for Treating Acute Myeloid Leukemia (AML)

Figure 1:
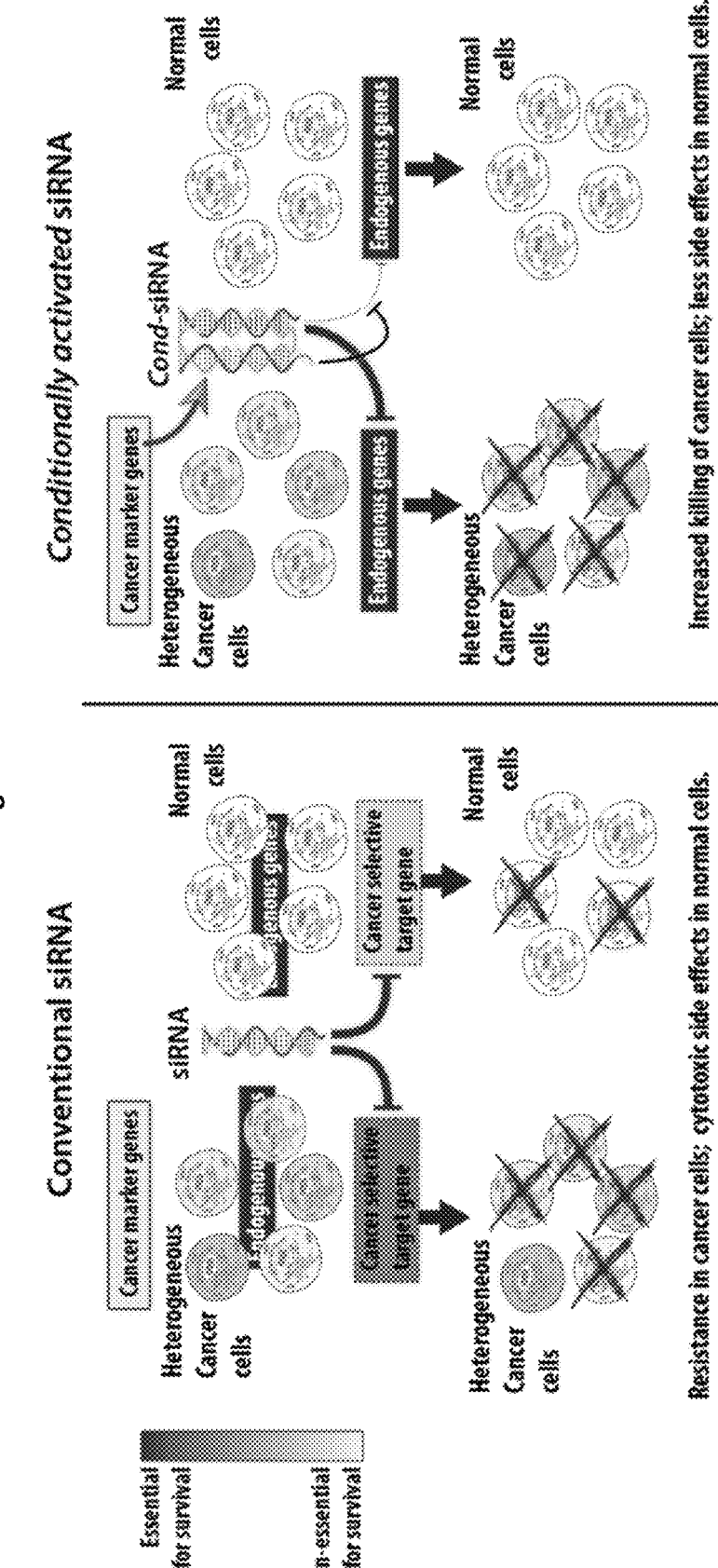
FIG. 1 shows the fundamental treatment concept for Conditionally activated-siRNAs (Cond-siRNAs).

Disclosed herein are approaches for attacking cancer cells lacking targetable survival essential mutations and resisting conventional therapies by selectively killing these cells using the RNA transcripts of mutated cancer genes to activate Cond-siRNAs targeting critical survival genes shared by cancer cells and normal cells. FIG. 1 shows the fundamental treatment concept for Cond-siRNAs and the use thereof for treating AML by killing AML cells using cell selective knock down of endogenous genes in cells that express AML associated oncogenes.

In one aspect, this disclosure relates to Cond-siRNAs that treat AML by inhibiting essential endogenous genes that express AML related fusion oncogenes. The construction and use of conditional-siRNAs programmable for activation by oncogenic transcription factors are shown in FIGS. 2A and 2B. Further details about the make and use of such constructs can be found in U.S. Pat. No. 9,725,715, entitled "Signal activatable constructs and related components com-positions methods and systems," the content of which is incorporated herein by reference in its entirety. In a related aspect, pharmaceutical compositions comprising such Cond-siRNAs and one or more pharmaceutically acceptable carrier or excipient are also disclosed herein. In another related aspect, disclosed are methods of treating AML in a subject comprising administering to the subject a therapeutically effective amount of the pharmaceutical composition comprising one or more Cond-siRNAs that detect CBFβ-MYH11 gene. In some embodiments, the Cond-siRNAs target and/or inhibit MCL-1. In some embodiments, the Cond-si RNAs target and/or inhibit HDAC8.

Figure 3:
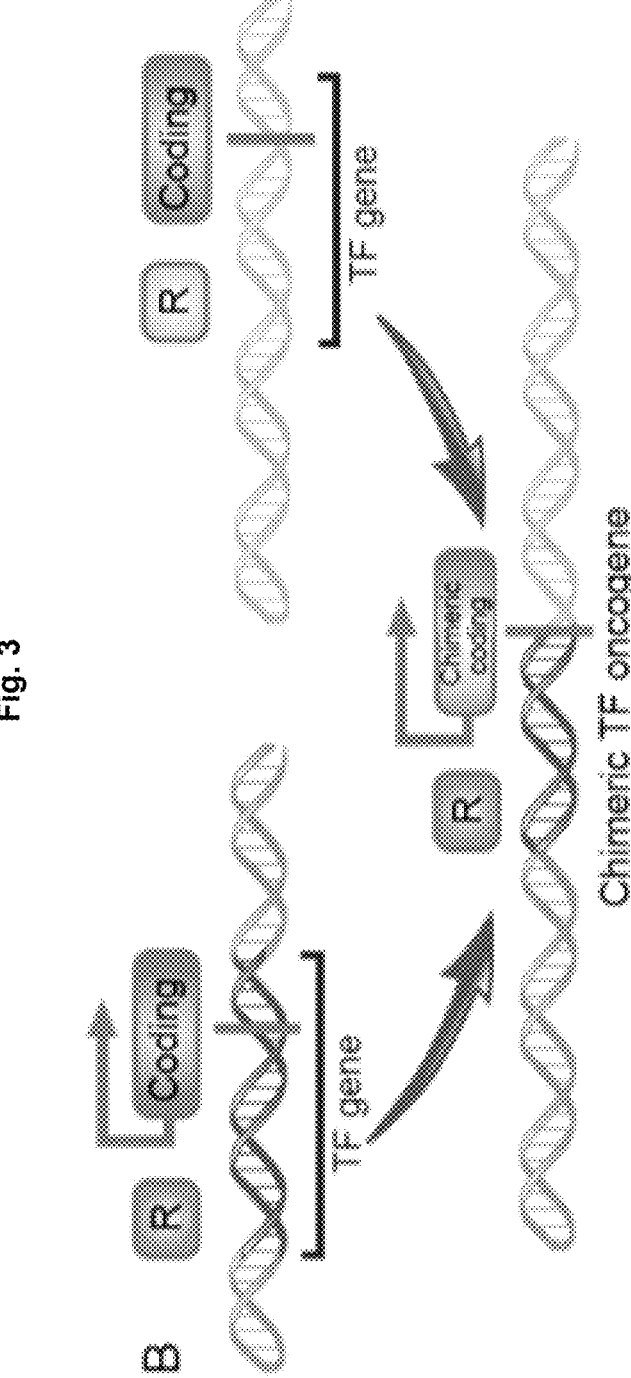
FIG. 3 illustrates the structure of fusion oncogenes (from reference 5).

In some embodiments, this disclosure relates to treating a subset of AML in which the fusion oncogene CBFβ-MYH11 was present. This chromosomal mutation is responsible for leukemogenesis and found in approximately 12% of AML patients.[5] This gene is created by a chromosome rearrangement that fuses the human CBFβ messenger RNA (mRNA) with the MYH11 mRNA (as shown in FIG. 3) at a specific point that is conserved across AML patients. While this mRNA is specifically expressed in AML cells, it is not essential for cancer cell survival. In some embodiments, the Cond-siRNAs can be activated by RNA transcripts from the CBFβ-MYH11 gene. To kill cancer cells, the Cond-siRNAs target HDAC8 or MCL-1. More detailed description can be found in Appendices B and C submitted herein, which are also included as part of this disclosure. For greater clarity, panels of Appendix A are shown in FIGS. 6-20.

Using conditional siRNA nanotechnology, an RNA nanostructure was constructed to recognize a specific sequence of the CBFβ-MYH11 gene, and to release an siRNA coding for the knockdown of MCL-1 mRNA. MCL-1 is an anti-apoptotic protein, necessary for the survival of hematopoietic stem cells and is essential for development and sustained growth of AML cells.[6] MCL-1 is an endogenous apoptosis inhibitor that is vital to the survival of hematopoietic stem cells and the maintenance of bone marrow.[7] Because of the importance of MCL-1 expression for AML cell survival, it is believed that knocking down MCL-1 mRNA in CBFβ-MYH11 AML cells will cause cancer cell death. In other embodiments, the Cond-siRNAs disclosed herein target HDAC8 to kill the cancer cells. The HDAC8 gene is a histone deacetylase that regulates transcription[8]. Inhibition of HDAC8 selectively kills AML cells[9].

Examples of Cond-siRNAs that detect CBFβ-MYH11 and inhibit either MCL-1 or HDAC8 have been developed and shown Appendices C and D.

In certain embodiments, the Cond-siRNAs complex may comprise a combination of the sensor strand, the core strand, and/or a guide strand selected from Table 1 below.

TABLE 1

| SEQ ID NOs. | STRAND | TARGET OR BIOMARKER | SEQUENCE |
|---|---|---|---|
| 1 | SENSOR | CBFb-MYH11 | 5' GACUTCTCCAGCUCAU GGACCTCCAUUUCCT 3' |
| 2 | GUIDE | MCL-1 | 5' GTCUUCUGCUAAUGGU UCGAUGCUU 3' |
| 3 | GUIDE | HDAC8 | ACACTTTCACAGATCTGGT |
| 4 | CORE | MCL-1 | 5' GCUGGAGAAGUC |
| 5 | | | linker GCAUCGAACCAU |
| 6 | | | UAGCAGAAGAC linker GAGGUCCAUGA 3' |

In another embodiment, the Cond-siRNAs complex may comprise a construct that includes a sensor strand corresponding to SEQ ID NO: 1, a Guide strand corresponding to SEQ ID NO:2, and a core strand corresponding to SEQ ID NO:3.

Methods of Treatment

The cond-siRNA complexes described above may be used in methods to treat AML. In other embodiments, a method for treating AML is disclosed herein, wherein the method includes a step of administering to a subject a therapeutically effective amount of one or more of the AML related cond-siRNAs described above. As disclosed herein, the subject may be any human or other animal suffering from AML.

"Treating" or "treatment" of a condition may refer to preventing the condition, slowing the onset or rate of development of the condition, reducing the risk of developing the condition, preventing or delaying the development of symptoms associated with the condition, reducing or ending symptoms associated with the condition, generating a complete or partial regression of the condition, or some combination thereof.

The methods for treating AML include administering a therapeutically effective amount of a therapeutic composition. An "effective amount," "therapeutically effective amount" or "effective dose" is an amount of a composition (e.g., a therapeutic composition or agent) that produces a desired therapeutic effect in a subject, such as preventing or treating a target condition or alleviating symptoms associated with the condition. The precise therapeutically effective amount is an amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, namely by monitoring a subject's response to administration of a compound and adjusting the dosage accordingly. For additional guidance, see Remington: The Science and Practice of Pharmacy 21st Edition, Univ. of Sciences in Philadelphia (USIP), Lippincott Williams & Wilkins, Philadelphia, P A, 2005.

In some embodiments, one or more cond-siRNAs may be used alone or as part of a pharmaceutical composition for treating AML. Thus, in some embodiments, a pharmaceutical composition comprising any one or more of the cardiac hypertrophy-related Cond-siRNAs described above is disclosed. In some embodiments, a pharmaceutical composition comprising any one or more of the AML-related Cond-siRNAs described above is disclosed. The therapeutic compositions may also include one or more pharmaceutically acceptable carriers. A "pharmaceutically acceptable carrier" refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or some combination thereof. Each component of the carrier must be "pharmaceutically acceptable" in that it must be compatible with the other ingredients of the formulation. It also must be suitable for contact with any tissue, organ, or portion of the body that it may encounter, meaning that it must not carry a risk of toxicity, irritation, allergic response, immunogenicity, or any other complication that excessively outweighs its therapeutic benefits.

The therapeutic compositions described herein may be administered by any suitable route of administration. A route of administration may refer to any administration pathway known in the art, including but not limited to aerosol, enteral, nasal, ophthalmic, oral, parenteral, rectal, transdermal (e.g., topical cream or ointment, patch), or vaginal. "Transdermal" administration may be accomplished using a topical cream or ointment or by means of a transdermal patch. "Parenteral" refers to a route of administration that is generally associated with injection, including infraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal.

Having described the invention with reference to the embodiments and illustrative examples, those in the art may appreciate modifications to the invention as described and illustrated that do not depart from the spirit and scope of the invention as disclosed in the specification. The examples are set forth to aid in understanding the invention but are not intended to, and should not be construed to limit its scope in any way. The examples do not include detailed descriptions of conventional methods. Such methods are well known to those of ordinary skill in the art and are described in numerous publications. Further, all references cited above and in the examples below are hereby incorporated by reference in their entirety, as if fully set forth herein. All appendices A-D submitted herewith constitute part of the complete disclosure.

EXAMPLES

Example 1: Design of Cond-siRNAs to Treat AMP

Figure 4:
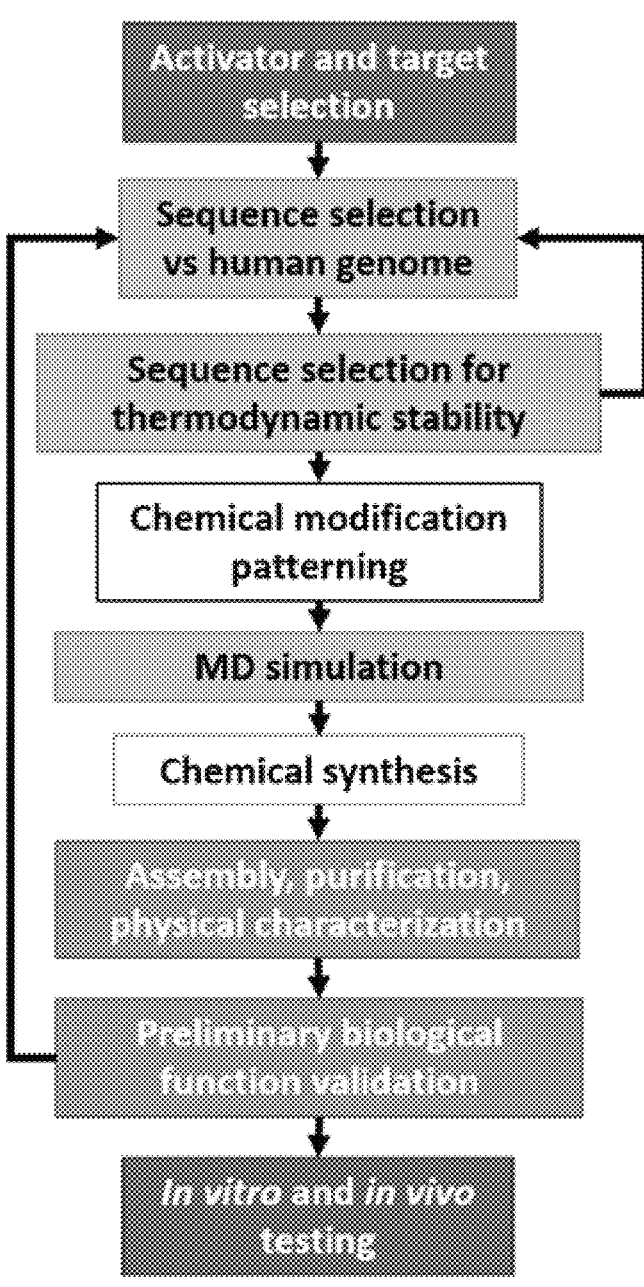
FIG. 4 shows the design and preliminary testing process for Cond-siRNAs.
Figure 5:
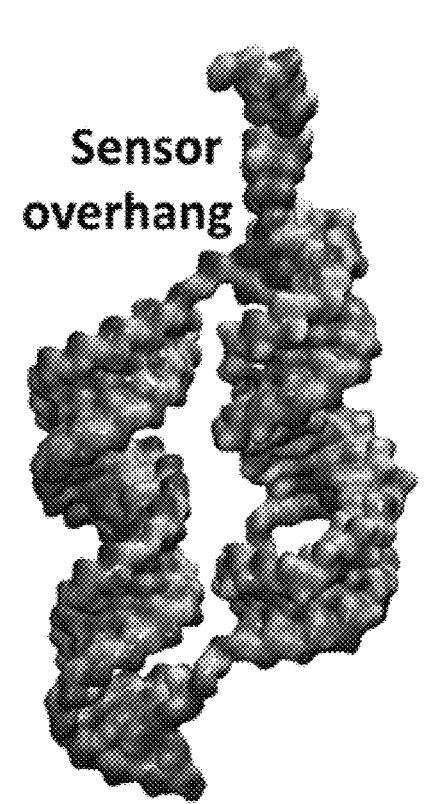
FIG. 5 shows an example of a computed model of Cond-siRNA via molecular dynamics simulation.
Figure 7:
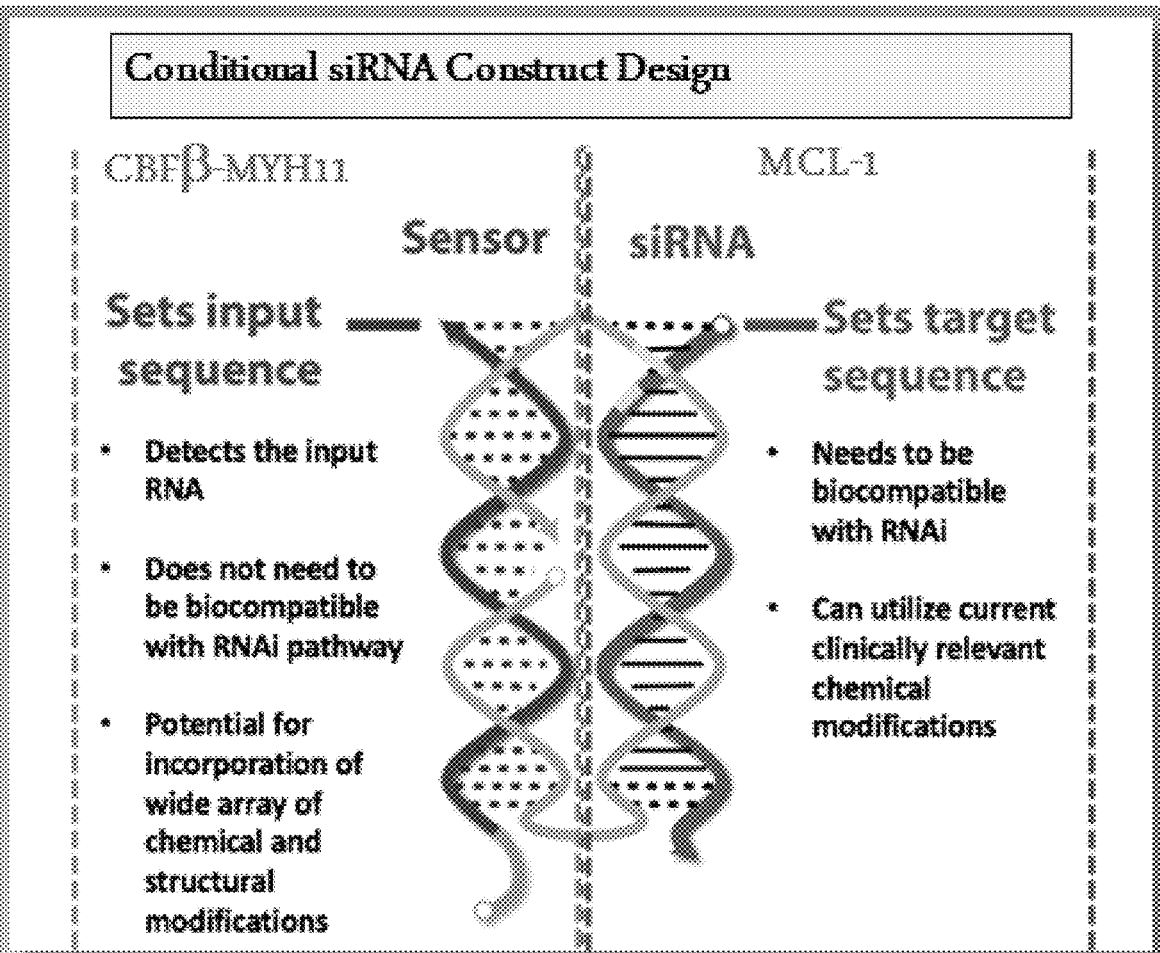
Figure 8:
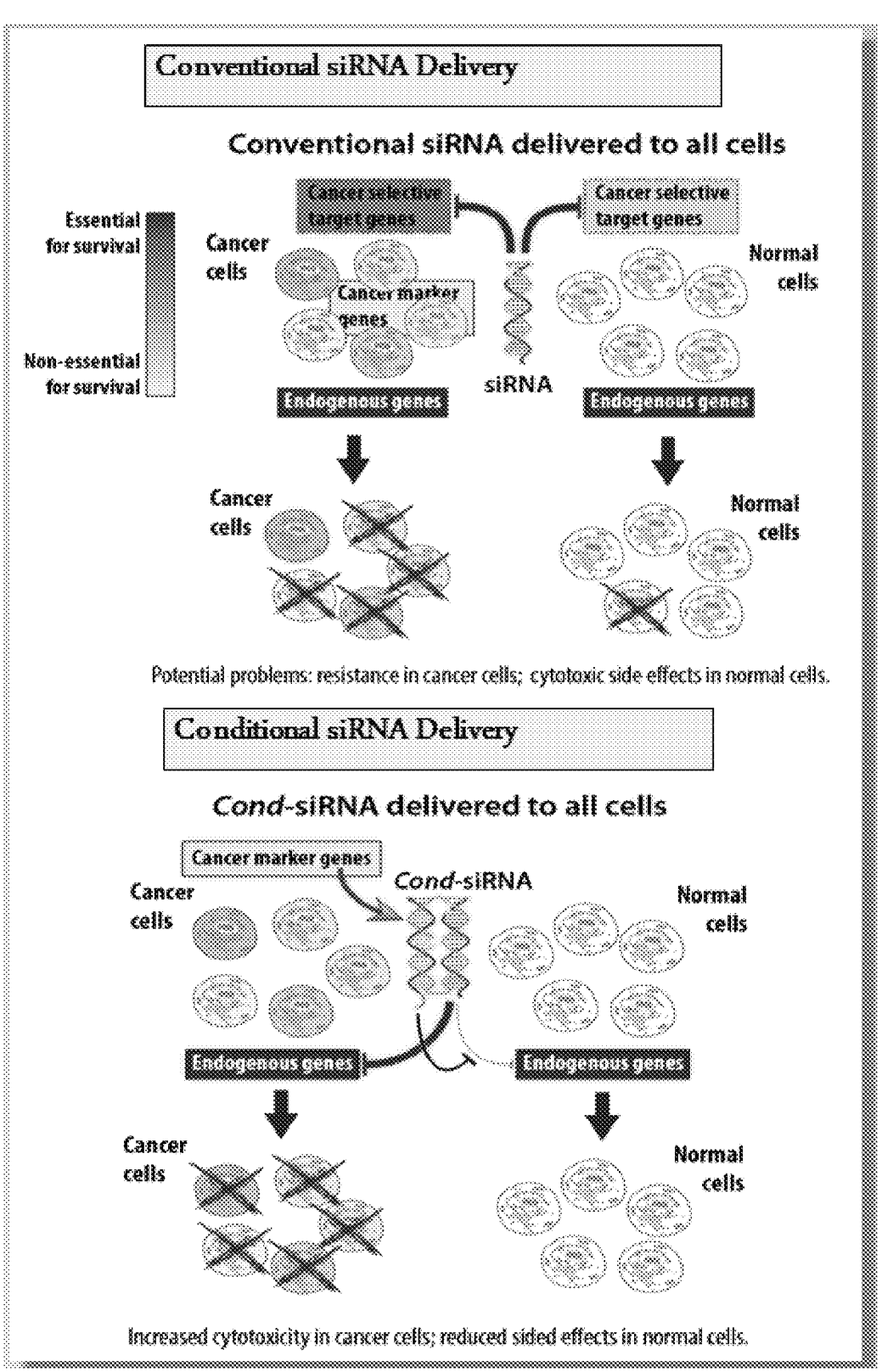

To design Cond-siRNAs for fusion oncogene activated knockdown of endogenous targets, a process of iterative design, testing and refinement as illustrated in FIG. 4 was followed. In this process, the activator (CBFβ-MYH11) and target (MCL-1) was selected in accordance with current knowledge on disease pathways. Then sensor and siRNA sequences were selected based on uniqueness in the human genome and thermodynamic stability of the resulting construct. Patterns of chemical modifications that support optimal functioning were used. Optionally, computational simulations were conducted to visualize the molecular conformation as illustrated in FIG. 5. Constructs with acceptable predicted conformations were sent for chemical synthesis by commercial vendors. Assembly and characterization of the Cond-siRNA were performed, followed by initial testing on HCT116 cells according to validated procedures. Construct design can then refined or pass on to disease model testing, depending on results.

Example 2: Design of Cond-siRNAs that Target MCL-1 and Activated by CBFβ-MYH11

The following experiment was conducted as follows: First, the Guide, Core and Sensor RNA strands are designed as follows:

MCL-1 guide strand. A Cond-siRNA complex was designed to include a sensor strand that includes the following sequence: GA+CU+TC+TCCAG+C UC+AUGGA+ CC+TC C+AUUU+C+C+T (SEQ ID NO:7). Chemical modifications can be made to the sensor strand, resulting in the following sensor strand sequence: /5Sp9/mG*mA*+C*m U*+T*mC*+T*mC*mC*mA*mG*+C*m U*mC*+A*m U*mG*mG*mA*+C*mC*+T*mC*mC*+A*mU*mU*mU*+C*+C*+T*/3AmMO/(SEQ ID NO:8)

Guide and Core Strands. The Cond-siRNA complex also includes a guide and core strand that are designed as follows:

The sequence of MCL-1 is found in Zhang et al, Oncogene (2011) 30, 1963-1968; doi:10.1038/onc.2010.559, then the CDS targeted siRNA was used to determine the MCL-1 target region—sense side, 2 different variants of MCL-1 human mRNA; sense side sequence below:

Aagct gcatcgaaccattagcaga aagtatcacaga c (SEQ ID NO:9)

Aagct gcatcgaaccattagcaga aagtat cacagac gttc (SEQ ID NO:10)

The guide strand exiqon, sequence is: /5AmMC6/+g+t cu u c u g c u a a ugguucgaugC uu(SEQ ID NO:11)

And the core strand is designed as follows: G*C*U*GGAGAAGUC C3*mG*mC*mAucgaacc auuagcaga aga*mc c3 GAGGUCCA*U*G*A (SEQ ID NO:12)

Sequences were checked by hand. The nucleotides and modifications are indacted as follows: (1)+A, +T, +C, +G are LNA; (2) mA, mU, mC, mG are 2'-O-methyl; (3) rA, rU, rC, rG are RNA; (3) * denotes phosphorothioate backbone connection; (4)/5Sp9/is a tri-ethylene glycol linker; (5)/iSpC3/is an internal C3 spacer; (6)/5AmMC6/is a 5' primary amine modification on a C6 linker; (7)/3AmMO/is a 3' primary amine modification.

The sensor sequence. The sensor sequence was designed to detect fusion oncogene CBFβ-MYH11, which is a fusion oncogene seen in 12% of AML cases.

The CBFβ-MYH11 sensor strand from prototype construct (SEQ ID NO: 13)
UCGGGAGGAAAUGGAGGUCCAUGAGCUGGAGAAGUCCAAGCGGGCCCUG

GAGACCCAGAUCGGGAGGAAAUGGAGGUCCAUGAGCUGGAGAAGUC

CBFb is bolded, MYH11 is italicized, and the toehold binding region underlined.

The MCL-1 siRNA target region from literature (Zhang et al, Oncogene (2011) 30, 1963-1968; doi:10.1038/onc.2010.559), corresponding to the MCL-1 target region in CDS of MCL-1 mRNA: Aagct gcatcgaaccattagcaga aagtatcacaga c (SEQ ID NO:9)

The Cond-siRNA complex is shown in Slide 9 of Appendix B.

The constructs are annealed and then gel purified, using electro-dialysis and subsequently quantified. FIG. 14.

Then, dual luciferase experiments were carried out for ON/OFF and activation. Experimental results are shown in FIG. 15-20 and Appendix A.

The OFF and preactivated ON cond-siRNAs constructs demonstrate a large differential target knockdown (up to ~20 fold at 1 nM) in our assays, providing a broad assay range that facilitates observation of activation.

In these experiments, a consistent two-fold activation was observed at 48 and 68 hours for the 1 nM concentration. Previous studies with similar constructs suggest that activation can be more readily observed by reducing background RNAi activity of the OFF constructs with more stringent purification and extending the time of activation.

Example 3: Testing in AML Cells

For testing on AML cell lines, Cond-siRNAs were delivered to mixed populations of AML/non-AML hematopoietic cells in suspension via lipid or (alternatively) electroporation based protocols. RNAi knockdown and selective cell killing are be measured and compared by Fluorescence Activated Cell Sorting (FACS), dual luciferase assays, Northern blots, Western blots and RT-PCR. See Appendix B, slide 12. Non-specific toxicity is measured by commercial assays for immune activation. Construct design is evolved iteratively until objectives outlined for phase one are achieved.

Treatment strategies using the complex described herein includes delivery of Cond-siRNAs broadly to myeloid cells, where they will enter AML blasts and stem cells to detect expression of CBFβ-MYH11 and consequently activate RNAi silencing of MCL-1. The leukemia blasts and stem cells would then be depleted by apoptosis. IN another alternative, Cond-siRNA against BCL-2 may be co-delivered to prevent resistance by compensatory expression of BCL-2. Other delivery strategies are shown in Slide 19 of Appendix A.

This strategy may also be viable for HIV to detect tat/rev HIV mRNA transcripts, and then inhibit MCL-1 to deplete the infected cells.

REFERENCES

1. "What are the key statistics about acute myeloid leuke-mia" American Cancer Society, 5 Jan. 2017, https://www.cancer.org/cancer/acute-myeloid-leukemia/about/key-statistics.html. Accessed 24 Jul. 2017.

2. Look, Thomas A. "Oncogenic Transcription Factors in the Human Acute Leukemias" Science, Vol. 278, Issue 5340, pp. 1059-1064

3. Glaser, Stefan P. et al. "Anti-apoptotic Mcl-1 is essential for the development and sustained growth of acute myeloid leukemia" Genes & Dev, Vol. 26 pp. 120-125

What is claimed is:

1. A conditional RNA-sensor complex comprising:
a sensor strand comprising at least one toehold segment, wherein the toehold segment binds a pathological biomarker that is associated with acute myeloid leukemia (AML) and present in or overexpressed in a target cell, wherein the sensor strand comprises a sequence having at least 95% homology to SEQ ID NO:1; and
a double stranded pro-siRNA molecule comprising
a guide strand comprising an RNA molecule that binds a therapeutic target molecule in the target cell, wherein the therapeutic target molecule is MCL-1 or HDAC8; and
a core strand comprising
a first portion comprising a passenger strand that is fully or partially complimentary to and binds the guide strand;
a second portion comprising a first protection segment that is fully or partially complimentary to and binds the sensor strand; and
a first linker that joins a first end of the passenger strand to the first protection segment.

2. The conditional RNA-sensor complex of claim 1, wherein the core strand further comprises a third portion comprising a second protection segment that is fully or partially complimentary to and binds the sensor strand, and a second linker that joins a second end of the passenger strand to the second protection segment.

3. The conditional RNA-sensor complex of claim 1, wherein the toehold segment is an aptamer.

4. The conditional RNA-sensor complex of claim 1, wherein the sensor strand is displaced from the double stranded pro-siRNA molecule when the pathological biomarker binds the toehold segment and the resulting double stranded pro-siRNA molecule is a substrate for Dicer.

5. The conditional RNA-sensor complex of claim 1, wherein the target cell is a cancer cell.

6. The conditional RNA-sensor complex of claim 5, wherein the pathological biomarker is a biomarker associated with acute myeloid leukemia (AML).

7. The conditional RNA-sensor complex of claim 6, wherein the pathological biomarker comprises a molecule that encodes a portion of CBFβ-MYH11.

8. The conditional RNA-sensor complex of claim 7, wherein the sensor strand comprises SEQ ID NO:1.

9. The conditional RNA-sensor complex of claim 7, wherein the guide strand comprises a sequence selected from SEQ ID NOS: 2-3.

10. The conditional RNA-sensor complex of claim 5, wherein the core strand comprises
a passenger strand;
a first linker that joins a 3' end of the passenger strand to the first protection segment; and a second linker that joins a 5' end of the passenger strand to the second protection segment.

11. The conditional RNA-sensor complex of claim 10, wherein the core strand comprises SEQ ID NOs: 4, 5 and 6.

12. The conditional RNA-sensor complex of claim 8, wherein the sensor strand, the guide strand and/or the core strand further comprises one or more chemical modifications to the RNA sequence, wherein the one or more chemical modifications are selected from a locked nucleic acid (LNA) modification, a peptide nucleic acid (PNA) modification, a 2'-O-methyl modification, morpholino modification, a phosphorothioate modification, a terminal modification, or a linker modification.

13. The conditional RNA-sensor complex of claim 1, wherein the core strand comprises a sequence having at least 95% homology to SEQ ID NOs: 4, 5 and 6, and the guide strand comprises a sequence having at least 95% homology to SEQ ID NO:2.

14. The conditional RNA-sensor complex of claim 13, wherein the sensor strand, the guide strand and/or the core strand further comprises one or more chemical modifications to the RNA sequence, wherein the one or more chemical modifications are selected from a locked nucleic acid (LNA) modification, a peptide nucleic acid (PNA) modification, a 2'-O-methyl modification, morpholino modification, a phosphorothioate modification, a terminal modification, or a linker modification.

15. The conditional RNA-sensor complex of claim 7, wherein the toehold segment is capable of binding to a least a portion of the sequence of SEQ ID NO: 13.

16. The conditional RNA-sensor complex of claim 7, wherein the pathological biomarker comprises the sequence of SEQ ID NO: 13.

17. A pharmaceutical composition comprising:
a conditional RNA-sensor complex of claim 1; and
a pharmaceutically acceptable carrier or excipient.

18. A method of treating a pathological condition comprising administering a therapeutically effective amount of a conditional RNA-sensor complex of claim 1 to a subject suffering from the pathological condition.

19. The method of claim 18, wherein the pathological condition is acute myeloid leukemia (AML).

\* \* \* \* \*

SEQUENCE LISTING

```
Sequence total quantity: 29
SEQ ID NO: 1            moltype = DNA   length = 31
FEATURE                Location/Qualifiers
misc_feature           1..31
                       note = sensor strand
source                 1..31
                       mol_type = other DNA
                       organism = synthetic construct
SEQUENCE: 1
gacttctcca gctcatggac ctccatttcc t                              31

SEQ ID NO: 2            moltype = DNA   length = 25
FEATURE                Location/Qualifiers
misc_feature           1..25
                       note = guide strand
source                 1..25
                       mol_type = other DNA
                       organism = synthetic construct
SEQUENCE: 2
gtcttctgct aatggttcga tgctt                                     25

SEQ ID NO: 3            moltype = DNA   length = 19
FEATURE                Location/Qualifiers
misc_feature           1..19
                       note = guide strand
source                 1..19
                       mol_type = other DNA
                       organism = synthetic construct
SEQUENCE: 3
acactttcac agatctggt                                            19

SEQ ID NO: 4            moltype = RNA   length = 12
FEATURE                Location/Qualifiers
misc_feature           1..12
                       note = core strand
source                 1..12
                       mol_type = other RNA
                       organism = synthetic construct
SEQUENCE: 4
gctggagaag tc                                                   12

SEQ ID NO: 5            moltype = RNA   length = 23
FEATURE                Location/Qualifiers
misc_feature           1..23
                       note = core strand
source                 1..23
                       mol_type = other RNA
                       organism = synthetic construct
SEQUENCE: 5
gcatcgaacc attagcagaa gac                                       23

SEQ ID NO: 6            moltype = RNA   length = 11
FEATURE                Location/Qualifiers
misc_feature           1..11
                       note = core strand
source                 1..11
```

-continued

```
                          mol_type = other RNA
                          organism = synthetic construct
SEQUENCE: 6
gaggtccatg a                                                          11

SEQ ID NO: 7             moltype = DNA  length = 31
FEATURE                  Location/Qualifiers
misc_feature             1..31
                         note = CBFbeta-MYH11 sensor
misc_feature             3
                         note = LNA
misc_feature             5
                         note = LNA
misc_feature             7
                         note = LNA
misc_feature             12
                         note = LNA
misc_feature             15
                         note = LNA
misc_feature             20
                         note = LNA
misc_feature             22
                         note = LNA
misc_feature             25
                         note = LNA
misc_feature             29..31
                         note = LNA
source                   1..31
                         mol_type = other DNA
                         organism = synthetic construct
SEQUENCE: 7
gacttctcca gctcatggac ctccatttcc t                                    31

SEQ ID NO: 8             moltype = DNA  length = 31
FEATURE                  Location/Qualifiers
misc_feature             1..31
                         note = Y3 sensor
misc_feature             1..31
                         note = phosphorothioate backbone connection
misc_feature             1..2
                         note = 2'-O-methyl
misc_feature             3
                         note = LNA
misc_feature             4
                         note = 2'-O-methyl
misc_feature             5
                         note = LNA
misc_feature             6
                         note = 2'-O-methyl
misc_feature             7
                         note = LNA
misc_feature             8..11
                         note = 2'-O-methyl
misc_feature             12
                         note = LNA
misc_feature             13..14
                         note = 2'-O-methyl
misc_feature             15
                         note = LNA
misc_feature             16..19
                         note = 2'-O-methyl
misc_feature             20
                         note = LNA
misc_feature             21
                         note = 2'-O-methyl
misc_feature             22
                         note = LNA
misc_feature             23..24
                         note = 2'-O-methyl
misc_feature             25
                         note = LNA
misc_feature             26..28
                         note = 2'-O-methyl
misc_feature             30..31
                         note = LNA
source                   1..31
                         mol_type = other DNA
                         organism = synthetic construct
SEQUENCE: 8
```

```
gacttctcca gctcatggac ctccatttcc t                                          31

SEQ ID NO: 9              moltype = DNA   length = 37
FEATURE                   Location/Qualifiers
source                    1..37
                          mol_type = other DNA
                          organism = Homo sapiens
SEQUENCE: 9
aagctgcatc gaaccattag cagaaagtat cacagac                                    37

SEQ ID NO: 10             moltype = DNA   length = 41
FEATURE                   Location/Qualifiers
source                    1..41
                          mol_type = other DNA
                          organism = Homo sapiens
SEQUENCE: 10
aagctgcatc gaaccattag cagaaagtat cacagacgtt c                               41

SEQ ID NO: 11             moltype = DNA   length = 25
FEATURE                   Location/Qualifiers
misc_feature              1..25
                          note = guide strand
misc_feature              1..2
                          note = LNA
source                    1..25
                          mol_type = other DNA
                          organism = synthetic construct
SEQUENCE: 11
gtcttctgct aatggttcga tgctt                                                 25

SEQ ID NO: 12             moltype = RNA   length = 48
FEATURE                   Location/Qualifiers
misc_feature              1..48
                          note = core strand
misc_feature              1..3
                          note = phosphorothioate backbone connection
misc_feature              13..15
                          note = phosphorothioate backbone connection
misc_feature              14..16
                          note = 2'-O-methyl
misc_feature              35
                          note = phosphorothioate backbone connection
misc_feature              36
                          note = 2'-O-methyl
misc_feature              45..47
                          note = phosphorothioate backbone connection
source                    1..48
                          mol_type = other RNA
                          organism = synthetic construct
SEQUENCE: 12
gctggagaag tccgcatcga accattagca gaagaccgag gtccatga                        48

SEQ ID NO: 13             moltype = RNA   length = 95
FEATURE                   Location/Qualifiers
misc_feature              1..95
                          note = CBFbeta-MYH11 sensor strand
misc_feature              65..76
                          note = CBFbeta
misc_feature              65..72
                          note = toehold binding region
misc_feature              77..95
                          note = MYH11
source                    1..95
                          mol_type = other RNA
                          organism = synthetic construct
SEQUENCE: 13
tcggaggaa atggaggtcc atagctgga gaagtccaag cgggccctgg agacccagat            60
cgggaggaaa tggaggtcca tgagctggag aagtc                                      95

SEQ ID NO: 14             moltype = DNA   length = 62
FEATURE                   Location/Qualifiers
source                    1..62
                          mol_type = other DNA
                          organism = Homo sapiens
SEQUENCE: 14
aggaaatgga ggtccatgag ctggagaagt caggaaatgg aggtccatga gctggagaag          60
tc                                                                          62

SEQ ID NO: 15             moltype = RNA   length = 31
```

-continued

```
FEATURE               Location/Qualifiers
misc_feature          1..31
                      note = MFE structure
source                1..31
                      mol_type = other RNA
                      organism = synthetic construct
SEQUENCE: 15
gacttctcca gctcatggac ctccatttcc t                                    31

SEQ ID NO: 16         moltype = DNA  length = 10
FEATURE               Location/Qualifiers
misc_feature          1..10
                      note = Y3 sensor
source                1..10
                      mol_type = other DNA
                      organism = synthetic construct
SEQUENCE: 16
ggaccccagg                                                            10

SEQ ID NO: 17         moltype = RNA  length = 25
FEATURE               Location/Qualifiers
misc_feature          1..25
                      note = guide strand
source                1..25
                      mol_type = other RNA
                      organism = synthetic construct
SEQUENCE: 17
gtcttctgct aatggttcga tgctt                                           25

SEQ ID NO: 18         moltype = DNA  length = 25
FEATURE               Location/Qualifiers
source                1..25
                      mol_type = other DNA
                      organism = Homo sapiens
SEQUENCE: 18
cgtcacactt tcacagatct ggtaa                                           25

SEQ ID NO: 19         moltype = RNA  length = 59
FEATURE               Location/Qualifiers
source                1..59
                      mol_type = other RNA
                      organism = Homo sapiens
SEQUENCE: 19
tcgggaggaa atggaggtcc atgagctgga gaagtccaag cgggccctgg agacccaga    59

SEQ ID NO: 20         moltype = DNA  length = 20
FEATURE               Location/Qualifiers
source                1..20
                      mol_type = other DNA
                      organism = Homo sapiens
SEQUENCE: 20
atggaggtcc atgagctgga                                                 20

SEQ ID NO: 21         moltype = DNA  length = 20
FEATURE               Location/Qualifiers
source                1..20
                      mol_type = other DNA
                      organism = Homo sapiens
SEQUENCE: 21
atggaggtcc gtgagctgga                                                 20

SEQ ID NO: 22         moltype = DNA  length = 15
FEATURE               Location/Qualifiers
source                1..15
                      mol_type = other DNA
                      organism = Homo sapiens
SEQUENCE: 22
aggtccatga gctgg                                                      15

SEQ ID NO: 23         moltype = RNA  length = 48
FEATURE               Location/Qualifiers
source                1..48
                      mol_type = other RNA
                      organism = Homo sapiens
SEQUENCE: 23
ggaggtccat gacaccagat ctgtgaaagt gtgacgccgg gaggaaat                 48

SEQ ID NO: 24         moltype = RNA  length = 31
FEATURE               Location/Qualifiers
```

-continued

```
source                  1..31
                        mol_type = other RNA
                        organism = Homo sapiens
SEQUENCE: 24
tctccagctc atggacctcc atttcctccc g                                    31

SEQ ID NO: 25           moltype = DNA  length = 31
FEATURE                 Location/Qualifiers
source                  1..31
                        mol_type = other DNA
                        organism = Homo sapiens
SEQUENCE: 25
tctccagctc atggacctcc atttcctccc g                                    31

SEQ ID NO: 26           moltype = DNA  length = 17
FEATURE                 Location/Qualifiers
source                  1..17
                        mol_type = other DNA
                        organism = Homo sapiens
SEQUENCE: 26
tcgggaggaa atggagg                                                    17

SEQ ID NO: 27           moltype = RNA  length = 48
FEATURE                 Location/Qualifiers
source                  1..48
                        mol_type = other RNA
                        organism = Homo sapiens
SEQUENCE: 27
gctggagaag tccaccagat ctgtgaaagt gtgacgcgag gtccatga                  48

SEQ ID NO: 28           moltype = RNA  length = 25
FEATURE                 Location/Qualifiers
source                  1..25
                        mol_type = other RNA
                        organism = Homo sapiens
SEQUENCE: 28
cgtcataaac actttaaaca ctggc                                           25

SEQ ID NO: 29           moltype = RNA  length = 46
FEATURE                 Location/Qualifiers
source                  1..46
                        mol_type = other RNA
                        organism = Homo sapiens
SEQUENCE: 29
gctggagaag tccagtgttt aaagtgttta tgacggaggt ccatga                    46
```